(12) United States Patent  
Blair

(10) Patent No.: US 8,354,931 B2
(45) Date of Patent: Jan. 15, 2013

(54) TRANSPONDER DEVICE TO MARK IMPLEMENTS, SUCH AS SURGICAL IMPLEMENTS, AND METHOD OF MANUFACTURING AND USING SAME

(75) Inventor: William A. Blair, San Diego, CA (US)

(73) Assignee: RF Surgical Systems, Inc., Redmond, WA (US)

( * ) Notice: Subject to any disclaimer, the term of this patent is extended or adjusted under 35 U.S.C. 154(b) by 647 days.

(21) Appl. No.: 12/536,384

(22) Filed: Aug. 5, 2009

(65) Prior Publication Data

US 2010/0033309 A1 Feb. 11, 2010

Related U.S. Application Data

(60) Provisional application No. 61/086,727, filed on Aug. 6, 2008, provisional application No. 61/220,452, filed on Jun. 25, 2009, provisional application No. 61/224,323, filed on Jul. 9, 2009.

(51) Int. Cl.
*G08B 13/14* (2006.01)

(52) U.S. Cl. ............... 340/572.8; 340/568.1; 340/572.1; 340/572.9; 340/10.1; 235/375; 235/385

(58) Field of Classification Search ............... 340/572.8, 340/505, 506, 508, 568.1, 572.1–572.9, 10.1–10.51; 235/375–385
See application file for complete search history.

(56) References Cited

U.S. PATENT DOCUMENTS

| | | | |
|---|---|---|---|
| 4,114,601 A | 9/1978 | Abels | 128/1 R |
| 4,193,405 A | 3/1980 | Abels | 128/296 |
| 5,057,095 A | 10/1991 | Fabian | 604/362 |
| 5,107,862 A | 4/1992 | Fabian et al. | 128/899 |
| 5,188,126 A | 2/1993 | Fabian et al. | 128/899 |
| 5,224,593 A | 7/1993 | Bennett | 206/5.1 |
| 5,329,944 A | 7/1994 | Fabian et al. | 128/899 |
| 5,456,718 A | 10/1995 | Szymaitis | 623/11 |
| 5,629,498 A | 5/1997 | Pollock et al. | 177/15 |

(Continued)

FOREIGN PATENT DOCUMENTS

WO 2006/060781 A1 6/2006

OTHER PUBLICATIONS

U.S. Appl. No. 12/046,396, filed Mar. 11, 2008.

*Primary Examiner* — George Bugg
*Assistant Examiner* — Sisay Yacob
(74) *Attorney, Agent, or Firm* — Seed IP Law Group PLLC

(57) ABSTRACT

A transponder device to mark a surgical implement, such as a metallic surgical instrument, is provided that comprises a transponder housing attachable to a portion of the surgical implement. The housing may include a transponder receiving cavity spaced at least 1 millimeter, and preferably at least 2 millimeters, from any portion of the surgical implement when the housing is attached to the surgical implement, and preferably includes a saddle-shaped finger support surface or a stabilizing surface sized and configured to receive a finger of a user for providing additional leverage and/or stabilizing structure when operating the implement. The housing may be removably attached to the surgical implement or permanently attached. In use, a transponder is retained in the device. Methods of manufacturing transponder devices and methods of detecting a transponder indicating the possible presence of a surgical implement are also provided.

44 Claims, 12 Drawing Sheets

U.S. PATENT DOCUMENTS

| | | | |
|---|---|---|---|
| 5,664,582 A | 9/1997 | Szymaitis | 128/898 |
| 5,923,001 A | 7/1999 | Morris et al. | 177/245 |
| 5,931,824 A | 8/1999 | Stewart et al. | 604/358 |
| 5,969,613 A | 10/1999 | Yeager et al. | 340/572.9 |
| 6,026,818 A | 2/2000 | Blair et al. | 128/899 |
| 6,276,033 B1 | 8/2001 | Johnson et al. | 24/704.1 |
| 6,366,206 B1 | 4/2002 | Ishikawa et al. | 340/573.1 |
| 6,734,795 B2 | 5/2004 | Price | 340/572.1 |
| 6,744,378 B1 * | 6/2004 | Tyburski | 340/933 |
| 6,778,089 B2 | 8/2004 | Yoakum | 340/572.8 |
| D502,419 S | 3/2005 | Copen | D10/104 |
| 6,861,954 B2 | 3/2005 | Levin | 340/572.1 |
| 6,998,541 B2 | 2/2006 | Morris et al. | 177/15 |
| 7,019,650 B2 | 3/2006 | Volpi et al. | 340/572.1 |
| D526,586 S | 8/2006 | McCaghren et al. | D10/65 |
| 7,118,029 B2 | 10/2006 | Nycz et al. | 235/375 |
| 7,135,973 B2 | 11/2006 | Kittel et al. | 340/568.2 |
| 7,135,978 B2 | 11/2006 | Gisselberg et al. | 340/572.5 |
| 7,142,118 B2 | 11/2006 | Hamilton et al. | 340/572.1 |
| D534,448 S | 1/2007 | Shaffer, II et al. | D10/104 |
| 7,158,754 B2 | 1/2007 | Anderson | 455/41.1 |
| 7,183,914 B2 | 2/2007 | Norman et al. | 340/568.1 |
| 7,183,927 B2 | 2/2007 | Kolton et al. | 340/572.8 |
| 7,307,530 B2 | 12/2007 | Fabian et al. | 340/572.1 |
| D568,186 S | 5/2008 | Blair et al. | D10/70 |
| 2002/0070863 A1 | 6/2002 | Brooking | 340/572.1 |
| 2003/0105394 A1 | 6/2003 | Fabian et al. | 600/407 |
| 2004/0129279 A1 | 7/2004 | Fabian et al. | 128/899 |
| 2004/0250819 A1 | 12/2004 | Blair et al. | 128/899 |
| 2004/0254420 A1 | 12/2004 | Ward | 600/37 |
| 2005/0049564 A1 * | 3/2005 | Fabian | 604/362 |
| 2005/0131397 A1 | 6/2005 | Levin | 606/1 |
| 2005/0247794 A1 * | 11/2005 | Jones et al. | 235/487 |
| 2006/0084934 A1 | 4/2006 | Frank | 604/362 |
| 2006/0106368 A1 | 5/2006 | Miller et al. | 606/1 |
| 2006/0202827 A1 | 9/2006 | Volpi et al. | 340/572.1 |
| 2007/0034670 A1 | 2/2007 | Racenet et al. | 227/180.1 |
| 2007/0038233 A1 | 2/2007 | Martinez et al. | 606/157 |
| 2007/0055109 A1 | 3/2007 | Bass et al. | 600/234 |
| 2007/0216062 A1 * | 9/2007 | Frank | 264/250 |
| 2007/0285249 A1 | 12/2007 | Blair et al. | 340/572.3 |
| 2008/0204245 A1 | 8/2008 | Blair et al. | 340/572.1 |
| 2008/0238677 A1 * | 10/2008 | Blair et al. | 340/572.1 |

* cited by examiner

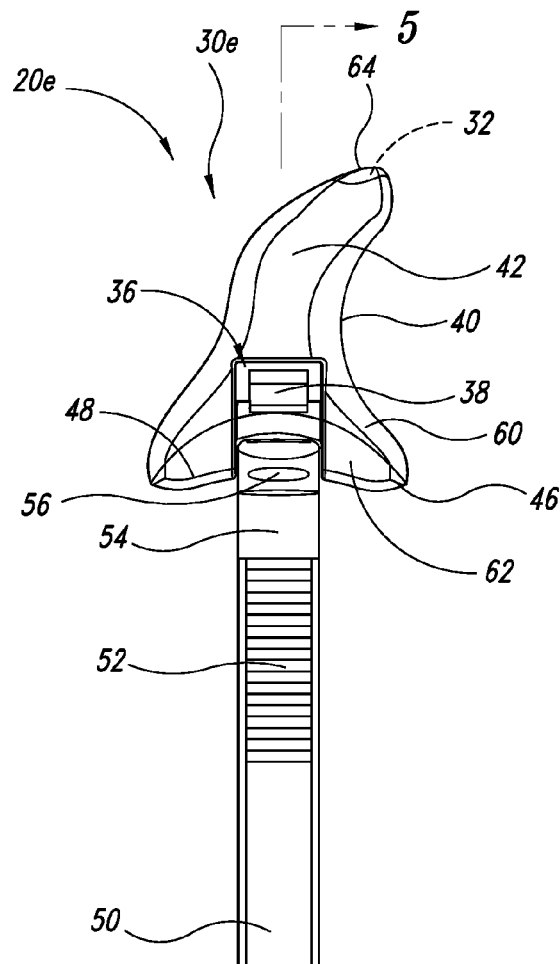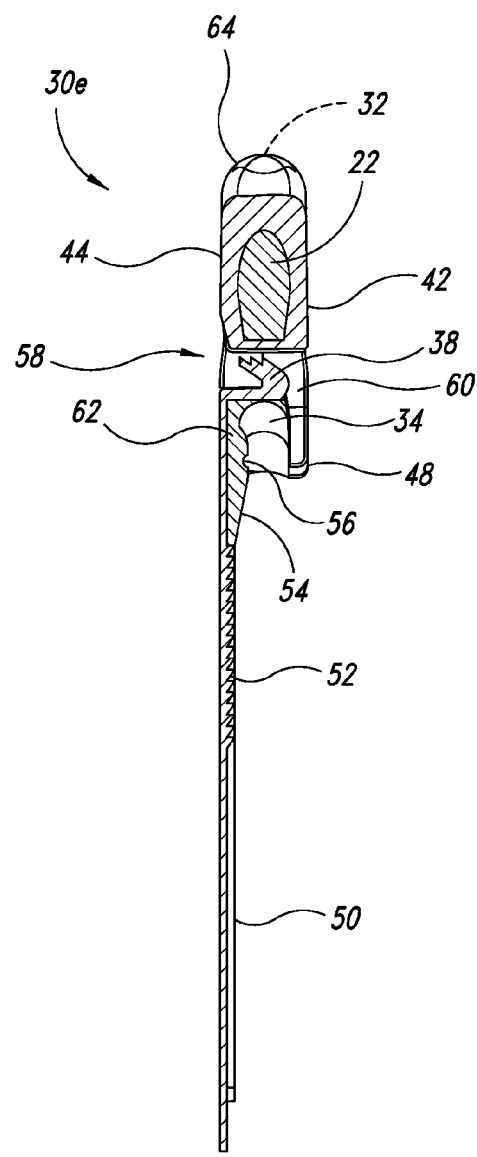
FIG. 4
FIG. 5

TRANSPONDER DEVICE TO MARK IMPLEMENTS, SUCH AS SURGICAL IMPLEMENTS, AND METHOD OF MANUFACTURING AND USING SAME

CROSS-REFERENCE TO RELATED APPLICATIONS

This application claims the benefit under 35 U.S.C. §119 (e) of U.S. Provisional Patent Application No. 61/086,727 filed Aug. 6, 2008; U.S. Provisional Patent Application No. 61/220,452 filed Jun. 25, 2009; and U.S. Provisional Patent Application No. 61/224,323 filed Jul. 9, 2009, where these (three) provisional applications are incorporated herein by reference in their entireties.

BACKGROUND

1. Technical Field

This disclosure generally relates to a device for marking rigid implements, such as surgical instruments.

2. Description of the Related Art

It is often useful or important to be able to determine the presence or absence of a foreign object.

For example, it is important to determine whether objects associated with surgery are present in a patient's body before completion of the surgery. Such objects may take a variety of forms. For example, the objects may take the form of instruments, for instance scalpels, scissors, forceps, hemostats, and/or clamps. Also for example, the objects may take the form of related accessories and/or disposable objects, for instance surgical sponges, gauzes, and/or pads. Failure to locate an object before closing the patient may require additional surgery, and in some instances may have serious adverse medical consequences.

Some hospitals have instituted procedures, which include checklists or requiring multiple counts to be performed to track the use and return of objects during surgery. Such a manual approach is inefficient, requiring the time of highly trained personnel, and is prone to error.

Another approach employs transponders and a wireless interrogation and detection system. Such an approach employs wireless transponders which are attached to various objects used during surgery. The interrogation and detection system may include a transmitter that emits pulsed wideband wireless signals (e.g., radio or microwave frequency) and a detector for detecting wireless signals returned by the transponders in response to the emitted pulsed wideband signals. Such an automated system may advantageously increase accuracy while reducing the amount of time required of highly trained and highly compensated personnel. Examples of such an approach are discussed in U.S. Pat. No. 6,026,818, issued Feb. 22, 2000, and U.S. Patent Publication No. US 2004/0250819, published Dec. 16, 2004.

Commercial implementation of such an automated system requires that the overall system be cost effective and highly accurate. In particular, false negatives must be avoided to ensure that objects are not mistakenly left in the patient. The overall automated system requires a large number of transponders, since at least one transponder is carried, attached or otherwise coupled to each object which may or will be used in surgery. Consequently, the transponders and devices for carrying, attaching or coupling the transponder to the object should be inexpensive. However, such inexpensive devices may hinder accurate detection. For instance, if the object and/or the device carrying the transponder is metallic or other metallic objects are present in the body, a transponder that is in fact present may not be able to be detected as a result of the metallic object acting as a Faraday shield or otherwise interfering with transponder communications. The transponder and/or device should be capable of undergoing sterilization. Consequently, an inexpensive device, for carrying, attaching, or coupling a transponder to a surgical implement quickly, reliably and securely is highly desirable.

BRIEF SUMMARY

At least one embodiment may be summarized as a device to mark surgical implements including a flexible strap; and a housing attachable to a portion of a surgical implement, the housing including a transponder receiving cavity sized to receive a transponder, an implement receiving cavity sized to receive a portion of the surgical implement, a strap receiving cavity sized to receive at least a portion of the strap, and a saddle-shaped finger support surface sized and configured to receive a finger of a user and provide additional leverage for operating the surgical implement when the housing is attached to the portion of the surgical implement via the strap and the implement receiving cavity. The housing may include a base substrate and a first overmold portion that forms the implement receiving cavity. The first overmold portion may include an indentation proximate a base of the strap where the strap is fixed to the housing such that a bend radius of the strap is reduced relative to an identically sized strap without an indentation. The first overmold portion may include a raised surface proximate a base of the strap that substantially conforms with a contour of a handle of the surgical implement when the housing is attached thereto. A projection of the first overmold portion may extend beyond an interior profile of a handle of the surgical instrument to provide a gradual transition from the interior profile of the handle to a surface of the strap when the housing is attached to the handle.

The device may further include the transponder, wherein the transponder is retained in the transponder receiving cavity. The housing may include a second overmold portion, the second overmold portion retaining the transponder within the transponder receiving cavity. The first overmold portion and the second overmold portion may include a material that is different from a material of the base substrate. The first overmold portion and the second overmold portion may each be composed of an elastomeric material. The strap receiving cavity may provide a void proximate a lower surface of the housing such that an end of the strap does not protrude beyond the lower surface when the strap is received in the strap receiving cavity and trimmed to a final length. The transponder receiving cavity may be spaced at least about 1 millimeter from any portion of the surgical implement when the housing is attached to the surgical implement via the strap. The strap and the housing may form a unitary structure.

At least one embodiment may be summarized as a transponder device including a housing having a base substrate and an overmold portion, the base substrate containing a transponder receiving cavity; attachment means for attaching the housing to a portion of a surgical implement; and a wireless transponder received in the transponder receiving cavity. The housing may position the wireless transponder at least 1 millimeter from the surgical implement when attached to the portion of the surgical implement. The overmold portion may retain the transponder in the base substrate. The overmold portion may include an implement receiving cavity.

The housing may further include a saddle-shaped finger support surface sized and configured to receive a finger of a user and provide additional leverage for operating the surgical implement when the housing is attached to the portion of the surgical implement via the implement receiving cavity. The overmold portion may include a first overmold location and a second overmold location, the first overmold location including an implement receiving cavity and the second overmold location retaining the transponder in the base substrate. The overmold portion may include a material different from a material of the base substrate. The overmold portion may be composed of an elastomeric material. The attachment means may include a strap and a detent mechanism that is integral to the housing. The overmold portion may include an indentation proximate a base of the strap where the strap is fixed to the housing such that a bend radius of the strap is reduced relative to an identically sized strap without an indentation. The overmold portion may include a raised surface proximate a base of the strap that substantially conforms with an interior contour of a handle of the surgical implement when the housing is attached thereto. The overmold portion may include an indentation in the raised surface such that a bend radius of the strap is reduced relative to an identically sized strap without an indentation. The overmold portion may include at least one projection extending beyond an interior profile of a handle of the surgical instrument to provide a gradual transition from the interior profile of the handle to a surface of the strap when the housing is attached to the handle.

The housing may further include a strap receiving cavity sized to receive at least a portion of the strap, the strap receiving cavity providing a void proximate a lower surface of the housing such that an end of the strap does not protrude beyond the lower surface when the strap is received in the strap receiving cavity and trimmed to a final length.

At least one embodiment may be summarized as a device to mark surgical implements including a rigid housing attachable to a portion of a surgical implement, the housing having a perimeter configured to accommodate at least an upper portion of a finger ring of the surgical implement and position a stabilizing surface to receive a finger of a user when operating the surgical implement; and a transponder retained in the housing and positioned such that the transponder is fixedly spaced at least about 1 millimeter from any portion of the surgical implement when the housing is attached to the surgical implement. The housing may further include a first surface and a second opposing surface, the second opposing surface being offset from the first surface such that a thickness of the housing is about equal to a thickness of the portion of the surgical implement. The stabilizing surface may include a concave portion sized and shaped to receive the finger of the user. The housing may be a rigid casing fabricated with the transponder enclosed therein. The housing may be a rigid shell structure having pre-existing cavities that cooperate to receive the transponder. The housing may be a rigid body having a pre-existing cavity sized to receive the transponder. The device may further include a strap for coupling the housing to the surgical implement. The device may further include an adhesive layer, the adhesive layer positioned on a portion of the perimeter of the housing to securely adhere the housing to the surgical implement when attached thereto.

At least one embodiment may be summarized as a device to mark surgical implements including a transponder and a unitary rigid housing attachable to a portion of a surgical implement, the housing having an implement receiving portion configured to engage an elongated handle portion of the surgical implement and a transponder receiving portion having the transponder received therein, the transponder receiving portion being configured with respect to the implement receiving portion to position the transponder substantially parallel to the elongated handle portion and fixedly space the transponder at least about 1 millimeter from any portion of the surgical implement when the housing is attached to the elongated handle portion of the surgical implement. The device may further include an elastomeric band, wherein the band is configured to encircle the elongated handle portion of the surgical implement and attach the housing to the surgical implement. The device may further include an adhesive layer, wherein the housing is attached to the elongated handle portion of the surgical implement via the adhesive layer. The transponder may be retained in the housing during fabrication of the housing. Alternatively, the transponder may be retained in the housing only after fabrication of the housing.

At least one embodiment may be summarized as a transponder device selectively attachable to surgical implements including a transponder circuit; a non-metallic framework that substantially encloses the transponder circuit, the framework having a number of outward extending projections; and a non-metallic body which at least partially surrounds the framework and which completely surrounds the transponder circuit, wherein the outward extending projections of the framework position the transponder circuit inwardly from an exterior surface of a mold used to form the body during a fabrication of the transponder device. The framework may include at least two pairs of opposed outward extending projections, one pair at each of a first and a second end of the framework. The framework may be completely received in the body. The device may further include an encapsulant that encapsulates the transponder circuit and which is surrounded by the framework. The device may further include a compliant overmold that interfaces with at least a first portion of the body. The compliant overmold may include an implement receiving cavity formed therein, the implement receiving cavity sized to at least partially receive a portion of a surgical implement. The framework may be a first shot of an injection molded material, the body may be a second shot of an injection molded material, and the compliant overmold that interfaces with at least a first portion of the body may be a third shot of an injection molded material. The third shot of injection molded material may be a different type of material from the second shot of injection molded material and may be an elastomeric material. The body of the transponder device may include a saddle-shaped finger support surface, the finger support surface sized and configured to receive a finger of a user and provide additional leverage to operate a surgical implement when the transponder device is attached to the surgical implement. The body may include an elongated strap extending therefrom, the strap dimensioned to encircle a portion of a surgical implement to attach the transponder device to the surgical implement. The body may also include a strap receiving cavity formed therein, the strap receiving cavity sized to receive at least a portion of the strap therethrough.

At least one embodiment may be summarized as a transponder device selectively attachable to surgical implements, the transponder device including a transponder circuit; a framework having a number of outward extending projections that space the transponder circuit from a surface that forms a cavity of a mold in the shape of a body; the body, which body at least partially surrounds the framework and which completely surrounds the transponder circuit; and a compliant overmold interfacing with at least a first portion of the body. The framework may be a first shot of an injection molded material, the body may be a second shot of an injection molded material, and the compliant overmold may be a third shot of an injection molded material. The body of the transponder device may include a saddle-shaped finger support surface, the finger support surface sized and configured to receive a finger of a user and provide additional leverage to operate a surgical implement when the transponder device is attached to a surgical implement. The body may include an elongated strap extending therefrom and a strap receiving cavity formed therein, the strap dimensioned to encircle a portion of a surgical implement and the strap receiving cavity sized to receive at least a portion of the strap therethrough, to attach the transponder device to the surgical implement. The compliant overmold may include an implement receiving cavity formed therein, the implement receiving cavity sized to at least partially receive a portion of a surgical implement.

At least one embodiment may be summarized as a method for manufacturing a device to mark implements including molding a base substrate, the base substrate including a transponder receiving cavity sized to receive a transponder, a flexible strap, a strap receiving cavity sized to receive at least a portion of the strap, and a saddle-shaped finger support surface sized to receive a finger of a user; inserting the transponder in the transponder receiving cavity; and retaining the transponder within the transponder receiving cavity. Retaining the transponder within the transponder receiving cavity may include retaining the transponder within the transponder receiving cavity by covering a portion of the transponder with a first overmold portion. Retaining the transponder within the transponder receiving cavity may include retaining the transponder within the transponder receiving cavity by covering the transponder with a cap. The method may further include forming an overmold portion with an implement receiving cavity such that a surface of the implement receiving cavity and the finger support surface converge proximate a tip of the device.

At least one embodiment may be summarized as a method for manufacturing a transponder device attachable to surgical implements including forming a non-metallic framework around a transponder circuit, the framework including a number of outward extending projections; retaining the framework in a mold cavity, wherein the outward extending projections of the framework position the transponder circuit inwardly from an exterior surface of the mold cavity; forming via the mold cavity a non-metallic body which at least partially surrounds the framework and which completely surrounds the transponder circuit; and forming a compliant overmold that interfaces with at least a first portion of the body, the compliant overmold including an implement receiving cavity sized to at least partially receive a portion of a surgical implement. The framework may be formed with a first shot of an injection molded material, the body may be formed with a second shot of an injection molded material; and the compliant overmold may be formed with a third shot of an injection molded material.

At least one embodiment may be summarized as a method including aligning a housing having a saddle-shaped finger support surface and a implement receiving cavity with a handle of each of one or more rigid surgical implements such that, when the handle is received in the implement receiving cavity, a wireless transponder enclosed within the housing is at least 1 millimeter from the handle, a central plane of the housing is substantially co-planar with a central plane of the handle, and the finger support surface is oriented to receive a finger of a user when the user is utilizing the surgical implement; and securing the housing onto the handle via a flexible strap. The method may further include transmitting a signal in a first frequency band during a first time proximate to a confined area; transmitting a signal in a second frequency band during a second time proximate to the confined area; receiving a response, if any, to the transmission of the signal in the first frequency band; and receiving a response, if any, to the transmission of the signal in the second frequency band. Securing the housing onto the handle via a flexible strap may include securing the housing onto the handle via a flexible strap using a tool. The method may further include trimming the flexible strap with a tool.

BRIEF DESCRIPTION OF THE SEVERAL VIEWS OF THE DRAWINGS

FIG. 4 is a front elevation view of the transponder device of FIG. 2.

FIG. 5 is a cross-sectional view of the transponder device of FIG. 2 taken along line 5-5 of FIG. 4.

DETAILED DESCRIPTION

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with transmitters, receivers, or transceivers, and types of surgical instruments have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The headings and Abstract of the Disclosure provided herein are for convenience only and do not interpret the scope or meaning of the embodiments.

For ease of understanding, a surgical environment will be used as an example environment for detecting implements but such should not be considered limiting.

Figure 1:
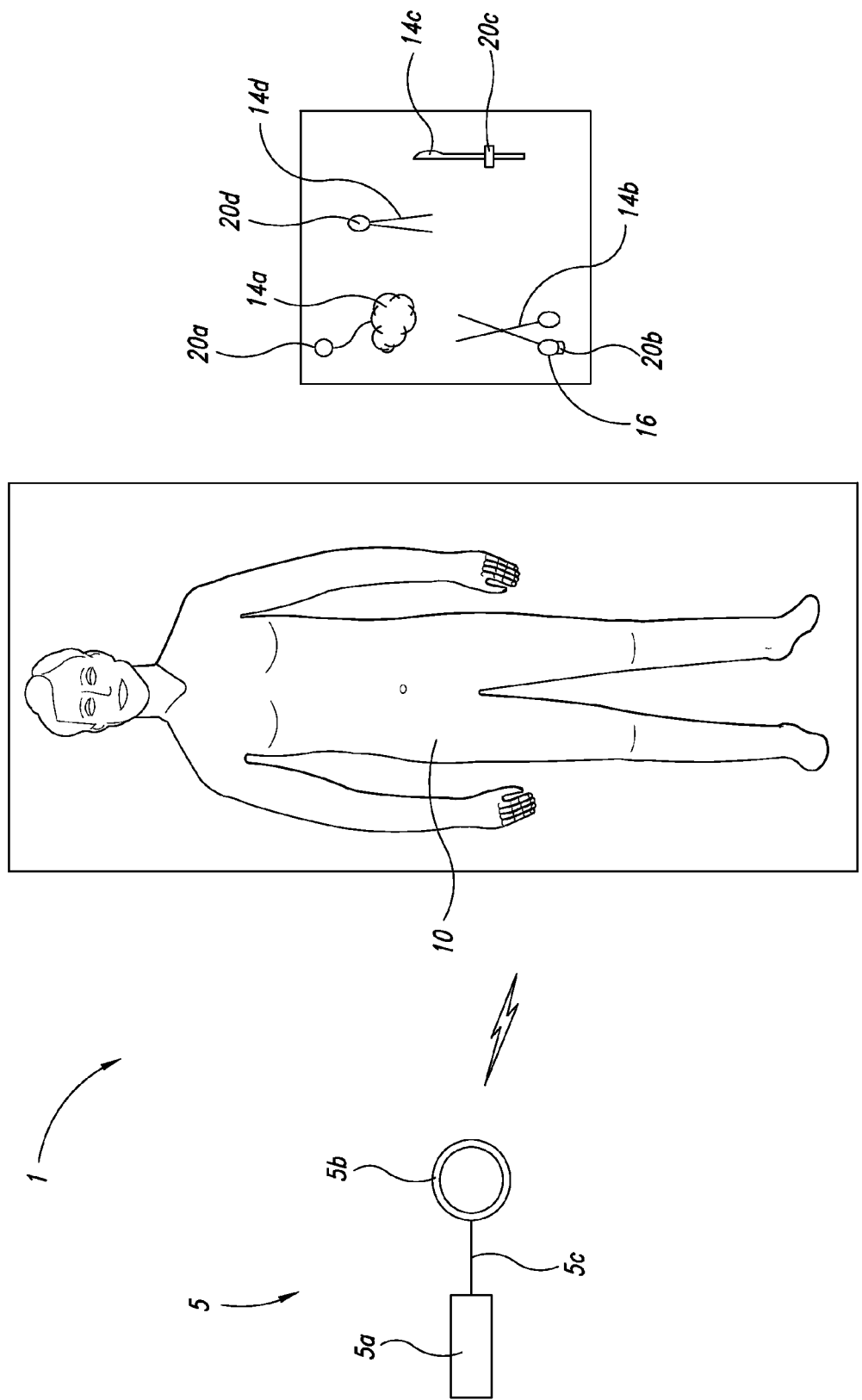
FIG. 1 is a schematic diagram showing a surgical environment illustrating use of an interrogation and detection system to detect one or more objects tagged with a transponder in a patient, according to one illustrated embodiment.
Figure 2:
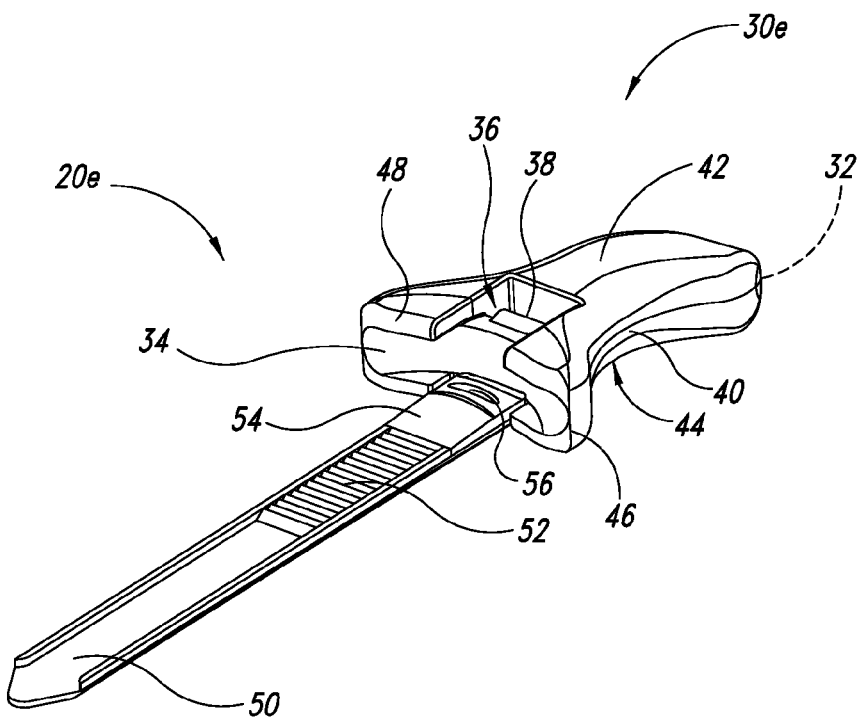
FIG. 2 is an isometric view of a transponder device according to one embodiment.
Figure 3:
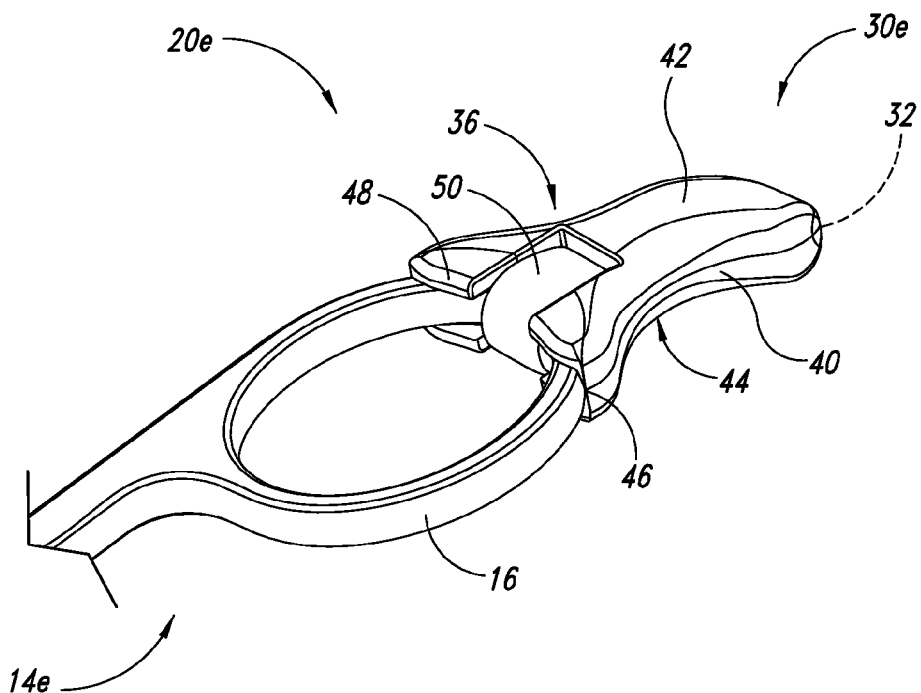
FIG. 3 is an isometric view of the transponder device of FIG. 2 attached to a surgical implement with a strap of the device trimmed.
Figure 6:
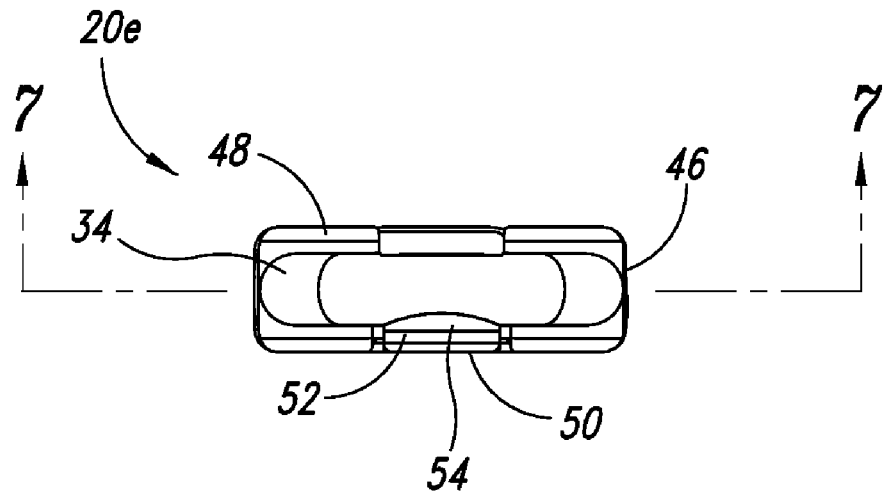
FIG. 6 is a bottom plan view of the transponder device of FIG. 2.

FIG. 1 shows a surgical environment 1 in which a medical provider (not shown) operates an interrogation and detection system 5 to ascertain the presence or absence of objects in, or on, a patient 10.

The interrogation and detection system 5 may include a controller 5a and an antenna 5b. The antenna 5b is coupled to the controller 5a by one or more communication paths, for example a coaxial cable 5c. The antenna 5b may take the form of a hand-held wand. The controller 5a is configured to cause the antenna 5b to emit wireless interrogation signals in one or more wide frequency bands, to receive responses from transponders to such interrogation signals, and to determine the presence or absence of a transponder based on the received responses, if any.

The surgical environment 1 may include a number of surgical implements, collectively 14. Surgical implements 14 may take a variety of forms, for example instruments, accessories and/or disposable objects useful in performing surgical procedures. Each surgical implement 14 is tagged with a transponder device, collectively 20. Thus, surgical implements 14a-14d may each be tagged with a respective transponder device 20a-20d. Examples of various transponder devices 20 may be found in U.S. patent application Ser. No. 12/046,396, filed Mar. 11, 2008.

Embodiments of the transponder device 20 disclosed herein include a housing 30 (FIGS. 2-8 and 13-17) that retains a transponder 22 (FIGS. 5, 7 and 10) and attaches or couples to the surgical implement 14. The transponder housing 30 carries the transponder 22 and spaces the transponder 22 from any metallic portion of the surgical implement 14 such that the surgical implement 14 does not interfere with wireless communications between the transponder 22 and the antenna 5b of the interrogation and detection system 5. The transponder 22 is typically small, for example approximately 5-10 millimeters long with a diameter of about 1-4 millimeters. In addition, in at least some embodiments, the transponder housing 30 advantageously protects the transponder from the ambient environment, for instance from forces, pressure and/or fluids, such as body fluids.

In some embodiments, the transponder 22 is received in the transponder housing 30 only after the transponder housing 30 is formed. In such embodiments, the transponder housing 30 may be a rigid shell structure with cavities formed therein for closing around the transponder 22 subsequent to fabrication of the shell structure or may include a rigid body having a pre-formed cavity for receiving a transponder 22 subsequent to fabrication of the body (as illustrated in FIGS. 2-7). The transponder 22 may be removably received in the housing 30 or fixed therein, for example, by enclosing the transponder 22 within the housing 30 with an overmold portion, as described in more detail below.

In other embodiments, the transponder housing 30 may be a rigid or semi-rigid casing or body enclosing the transponder 22, wherein the casing or body is fabricated with the transponder 22 retained therein during at least a portion of the fabrication process that forms the transponder housing 30 (as illustrated in FIGS. 8 and 13-17). As used herein, fabrication does not include the coupling together of previously fabricated portions of the transponder housing, but rather refers to the actual manufacture of those portions, whether by molding (e.g., injection molding, roto-molding), pressing, or other forms of fabrication.

Embodiments of the transponder device 20 disclosed herein are particularly suited to operate with metallic implements, and more particularly metallic implements having a manipulable handle 16 for operating the implement during surgery or the like. As used in this specification and the appended claims, a metallic implement, such as surgical implements, may be made partially or wholly of metal, so long as the implement could act, alone or in association with other metallic objects, as a Faraday shield or otherwise interfere with communications between the transponders 22 and the interrogation and detection system 5. Examples of various types of metallic implements include, but are not limited to, cutting instruments (e.g., a scalpel 14c, lancet, knife, scissors), grasping instruments (e.g., tweezers 14d, forceps), clamping instruments (e.g., hemostat 14b, clamps), instruments to provide access or expand tissue (e.g., dilators, specula), injection/irrigation instruments (e.g., needles, tips), drilling instruments (e.g., a drill bit and/or drill), or measurement instruments (e.g., rulers, calipers). In addition, to the metallic surgical implements, other surgical implements may also be tagged and identified for use with the interrogation and detection system, such as a sponge 14a. In some embodiments, some or all of those surgical implements are tagged using other types of transponder devices or attachment structures.

In use, the medical provider (not shown) may position the antenna 5b proximate the patient 10 in order to detect the presence or absence of the transponder 22 and hence a foreign metallic object. The medical professional may in some embodiments move the antenna 5b along and/or across the body of the patient 10. In some embodiments, the antenna 5b may be sized to fit at least partially in a body cavity of the patient 10. Different types of transponders 22 may be used in the various transponder housings 30. Although a human patient 10 is illustrated, the described interrogation and detection system 1 may similarly be used on animals.

FIGS. 2-7 illustrate a transponder device 20e for attaching to a portion of a handle 16 (FIG. 3) of a surgical implement 14e (FIG. 3), according to one embodiment.

The transponder device 20e is advantageously attached to a portion of a handle 16 of a surgical implement 14e such that the transponder device 20e does not physically interfere with the operation of the surgical implement 14e. The transponder device 20e includes a transponder housing 30e having a body with a transponder receiving cavity 32 and an implement receiving cavity 34 that is sized, dimensioned and otherwise configured to receive a portion of the handle 16 of the surgical implement 14e.

In one embodiment, the transponder receiving cavity 32 is preformed and preexisting in the body of the housing 30e, that is the transponder receiving cavity 32 exists independent of the presence or existence of a transponder 22. Thus, the housing 30e may be produced or manufactured separately from the transponder 22, which may later be loaded into the transponder receiving cavity 32, and possibly subsequently removed therefrom.

The transponder receiving cavity 32 is located such that the transponder 22 is spaced at least about 1 millimeter and preferably at least about 2 millimeters from any metallic portion of the surgical implement 14e when the transponder housing 30e is attached or otherwise coupled to the surgical implement 14e. Advantageously, if the surgical implement 14e is metallic, the distance helps to prevent signal loss due to the metallic implement acting as a Faraday shield or otherwise interfering with wireless communications of the transponder 22.

Figure 7:
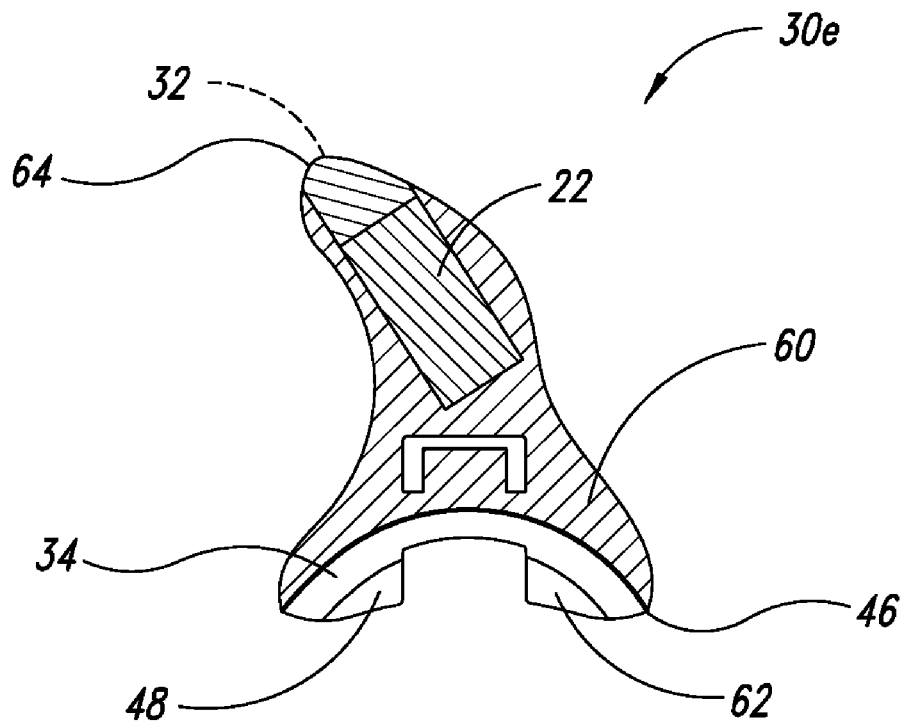
FIG. 7 is a cross-sectional view of the transponder device of FIG. 2 taken along line 7-7 of FIG. 6.

The transponder receiving cavity 32 may be asymmetrically positioned within the transponder housing 30e to achieve the desired separation of the transponder 22 from the surgical implement 14e in a reduced or minimal form factor or package. For example, the transponder receiving cavity 32 may be formed in the transponder housing 30e oriented at an angle as illustrated in FIG. 7. The reduced or minimal form factor or package enables the transponder housing 30e to attach or couple to the surgical implement 14e without intervening or interfering with movement of adjacent structures of the surgical implement 14e.

The transponder 22 may be constructed in various manners. For example, the transponder 22 may include a ferrite rod with a conductive coil wrapped about an exterior surface thereof to form an inductor, and a capacitor coupled to the conductive coil to form a series circuit. The conductive coil may, for example, take the form of a spiral wound conductive wire with an electrically insulative sheath or sleeve. Additional details about types of transponders may be found in U.S. patent application Ser. No. 11/759,141, filed Jun. 6, 2007 and U.S. patent application Ser. No. 12/038,593, filed Feb. 27, 2008.

The transponder housing 30e further includes one or more structures to accommodate a user's (e.g., surgeon or assistant) fingers or other body parts, such as an arcuate or concave finger receiving structure. The illustrated embodiment includes a finger receiving structure in the form of a saddle-shaped finger support surface 40. The finger support surface 40 is located on a side of the housing 30e and provides a continuous transition from an upper housing surface 42 to a lower housing surface 44 to comfortably receive a user's finger. The finger support surface 40 converges with the implement receiving cavity 34 proximate a tip 46 of the transponder housing 30e. The finger support surface 40 enables a user's finger to be received in close proximity to the handle 16 of the surgical implement 14e and assists operation thereof by increasing leverage on the handle 16 and providing additional means for stabilizing and controlling the surgical implement 14e.

The transponder housing 30e further includes a strap receiving cavity 36 sized and shaped to receive a portion of a flexible strap 50 of the transponder device 20e. The strap 50 may be formed as an integral or a unitary portion of the transponder housing 30e, or may be separate or distinct therefrom. The strap 50 is adapted to secure the transponder housing 30e to the surgical implement 14e via attachment mechanisms or structures, the attachment mechanisms or structures including an engagement structure on the strap 50, such as, for example, teeth 52, detents, barbs, snaps, or the like, and a complimentary engagement structure on the housing 30e. In one embodiment, the strap 50 and strap receiving cavity 36 of the transponder housing 30e cooperate to form a detent mechanism wherein a pawl 38 within the strap receiving cavity 36 engage teeth 52 on the strap 50 to securely attach the transponder housing 30e to the surgical implement 14e. The strap 50 may be selectively tightened around a portion of the surgical implement 14e by passing the strap 50 through the strap receiving cavity 36 and applying a tensile force to the end of the strap 50. The strap 50 may be fixedly or removably secured to the transponder housing 30e and may be attached manually or with the aid of a tool (not shown).

The strap 50 may include additional features to facilitate secure engagement of the transponder housing 30e with the surgical implement 14e. For example, the strap 50 may include a raised surface 54 proximate a base of the strap 50 that substantially conforms with a contour of the handle 16 of the surgical implement 14e when the transponder housing 30e is attached thereto. This allows the strap 50 to closely engage the handle 16 and help restrain the housing 30e from shifting on the handle 16. As another example, the strap 50 may include an indentation 56 proximate a base of the strap 50 where the strap 50 is fixed to the housing 30e such that a bend radius of the strap 50 is reduced relative to an identically sized strap without an indentation. This feature also facilitates close engagement of the strap 50 and handle 16.

After engagement with the transponder housing 30e, the strap 50 is preferably trimmed to length to avoid interfering with the operation of the surgical implement 14e and to prevent inadvertent contact with the user. The strap receiving cavity 36 of the transponder housing 30e preferably includes a void 58 proximate the lower surface 44 of the transponder housing 30e, such that the end of the strap 50 does not protrude beyond the lower surface 44 when trimmed to a final length. This prevents inadvertent injury caused by any sharp edges that may be present on the strap 50 subsequent to trimming.

In an attached configuration (FIG. 3), the strap 50 encircles the handle 16 of the surgical implement 14e and therefore interrupts a portion of the interior profile of the handle 16. To minimize any discomfort a user may encounter from the strap 50, one embodiment of the transponder housing 30e includes one or more projections 48 that extend beyond the interior profile of the handle 16 to provide a gradual transition from the interior profile to a surface of the strap 50. In another embodiment, the strap 50 may be composed of a semi-rigid material to improve user comfort during operation or may include additional protection means, such as, for example, an area of soft, pliant material where the user contacts the strap 50 during use.

The transponder device 20e may be constructed or formed using a variety of known manufacturing techniques, such as, for example, injection molding. The transponder device 20e may be molded in a single step such that the transponder housing 30e and the strap 50 are integral and formed of the same material. A transponder 22 may be supplied prior to molding to be encapsulated or encased in the transponder device or may be inserted in the preformed transponder receiving cavity 32 subsequent to molding.

The transponder receiving cavity 32 may be sized to snugly receive at least a portion of the transponder 22, for example with a friction or interference fit. The transponder receiving cavity 32 may include clips or other resilient structures for retaining the transponder 22 when received therein. In one embodiment, the transponder 22 may be glued in the transponder receiving cavity 32. In yet another embodiment, a cap (not shown) may be provided for sealing the transponder 22 in the transponder receiving cavity. The cap may be formed integrally with the housing 30e or may be separate and distinct therefrom.

The transponder device 20e may be manufactured using a multimaterial molding process, such as an overmolding process. The transponder device 20e may be formed by the acts of: molding a base substrate 60, wherein the base substrate 60 includes a transponder receiving cavity 32 sized to receive a transponder 22, a flexible strap 50, a strap receiving cavity 36 sized to receive at least a portion of the strap 50, and a saddle-shaped finger support surface 40 sized to receive a finger of a user; inserting the transponder 22 in the transponder receiving cavity 32; and retaining the transponder 22 within the transponder receiving cavity transponder 32 with an overmold portion 64. In some embodiments, the resultant base substrate 60 is a rigid material and the overmold portion 64 is formed of an elastomeric material.

A rigid base substrate 60 ensures that the transponder 22 is appropriately spaced from the surgical implement 14e without regard to the orientation (e.g., with respect to gravity) of the surgical implement 14e and/or without regard to forces or pressures that may be asserted on or through the surgical implement 14e and/or base substrate 60. Various materials may be used to make a rigid, preferably non-metallic, base substrate 60, for example various plastics, nylons or glasses. Since it is advantageous to reuse the transponder housing 30e to reduce costs, it is desirable to make the base substrate 60 and any overmold portion out of a material that is able to withstand multiple sterilizations, such as by autoclaving the transponder housing 30e or exposing the transponder housing 30e to ultraviolet (UV) light or chemical sanitizers. For example, the base substrate 60 and any overmold portion may be made out of bio-inert, high service temperature plastic, such as those made under the trade names KRATON G® or PROFAX® polypropylene homopolymer.

In one embodiment, the transponder device 20e is formed in an overmolding process such that the transponder housing 30e includes a base substrate 60, a first overmold portion or location 62 and a second overmold portion or location 64. The first overmold portion 62 preferably forms an implement receiving cavity 34, a raised surface 54, an indentation 56, and one or more projections 48, as best shown in FIG. 5. The first overmold portion 62 may be resilient such that it partially deforms when engaging the surgical implement 14e, thus ensuring a more secure fit and preventing the housing 30e from shifting on the handle 16. The second overmold portion 64 may be formed of a same or a different material than the first overmold portion 62. The second overmold portion 64 is applied to an end of the transponder receiving cavity 32 subsequent to placement of a transponder 22 therein to retain the transponder 22 in the housing 30e. The second overmold portion and/or first overmold portion may further include indication features, such as markings or color, that correlate to and indicate the type of transponder 22 retained in the housing 30e.

As illustrated in FIGS. 8-11, and according to another embodiment, a transponder device 20k may be formed in a multi-stage fabrication process wherein a transponder 22 is retained in a rigid or semi-rigid non-metallic framework 110 prior to formation of a body 33 of the transponder housing 30k. The framework 110 substantially encloses the transponder 22 and includes a number of outward extending projections (collectively 120) for spacing the transponder 22 inwardly from an exterior surface 136 of a cavity 131 of a mold 130 that is used to form the body 33 of the transponder housing 30k. As such, the transponder 22 is fixedly positioned in an interior region of the body 33 of the housing 30k of the transponder device 20k.

More particularly, the illustrated framework 110 is elongated having a first end 112 and a second end 114. A first set of outward extending projections 120a, including two pairs of opposing projections, is located at the first end 112 to position the first end 112 of the framework 110 in an upper portion 132 of the mold cavity 131. A second set of outward extending projections 120b, including a pair of opposing projections, is located at the second end 114 to position the second end 114 of the framework 110 in a mid-portion 134 of the mold cavity 131. The projections 120 thereby collectively position the transponder 22 within an interior region of the mold cavity 131 (i.e., inwardly from an exterior surface 136 of the mold cavity 131). As such, once the body 33 of the housing 30k is formed, the body 33 completely surrounds the transponder 22. In this manner, the transponder housing 30k is fabricated with the transponder 22 retained in the housing 30k at the time of fabrication of the housing 30k, which is in contrast to other embodiments described herein wherein the transponder may be supplied separate from and subsequent to fabrication of a transponder housing.

Figure 11:
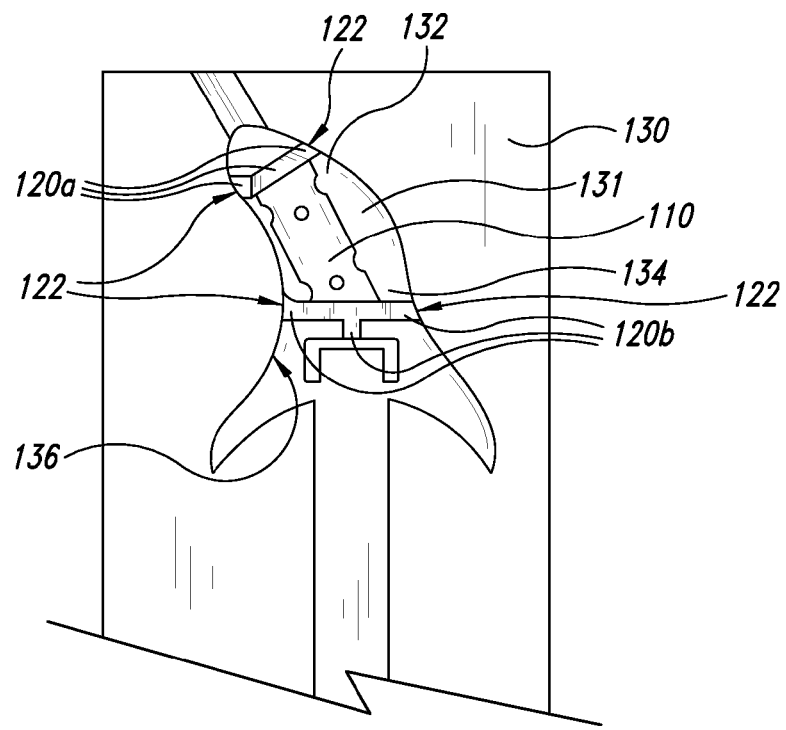
FIG. 11 is a top plan view of the framework of FIG. 9 retained in a mold cavity.

As can be appreciated from FIG. 11, a number of the projections 120 of the framework 110 extend to an exterior surface 136 of the mold cavity 131 such that, when the mold cavity 131 is used to fabricate the body 33 of the housing 30k, an end surface 122 of each such projection is substantially coextensively aligned with an outer surface of the resultant body 33 of the housing 30k. Accordingly, the resultant body 33 partially surrounds the framework 110 with one or more end surfaces 122 of the framework 110 forming a portion of the exterior surface of the transponder device 20k. In other embodiments, the framework 110 may be completely received in the body 33 such that no portion of framework 110 is visible to a user of the transponder device 20k.

Figure 10:
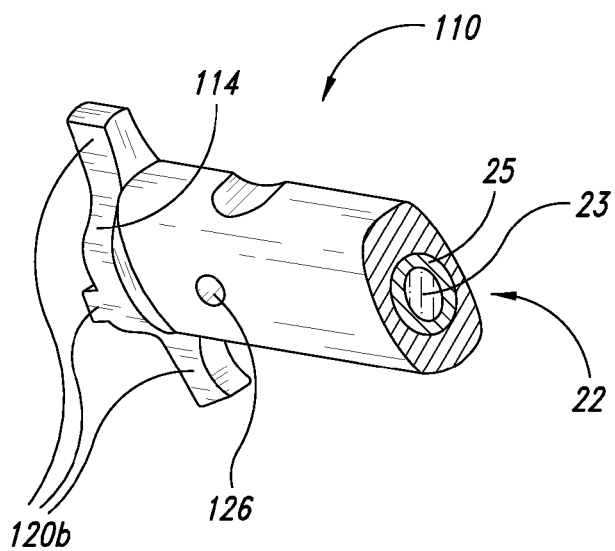
FIG. 10 is a cross-sectional view of the framework of FIG. 9.

As illustrated in FIG. 10, the transponder 22 may comprise a transponder circuit 23 and an encapsulant 25 that encapsulates the transponder circuit 23. Consequently, when the framework 110 is formed around the transponder 22, the framework 110 may completely surround the transponder circuit 23 and the encapsulant 25 or may substantially enclose the same. For example, in the illustrated embodiment of FIG. 9, except for a number of small apertures 126 that result from the use of locating pins to position the transponder 22 during fabrication of the framework 110, the transponder 22 is otherwise completely surrounded by the framework 110.

Figure 8:
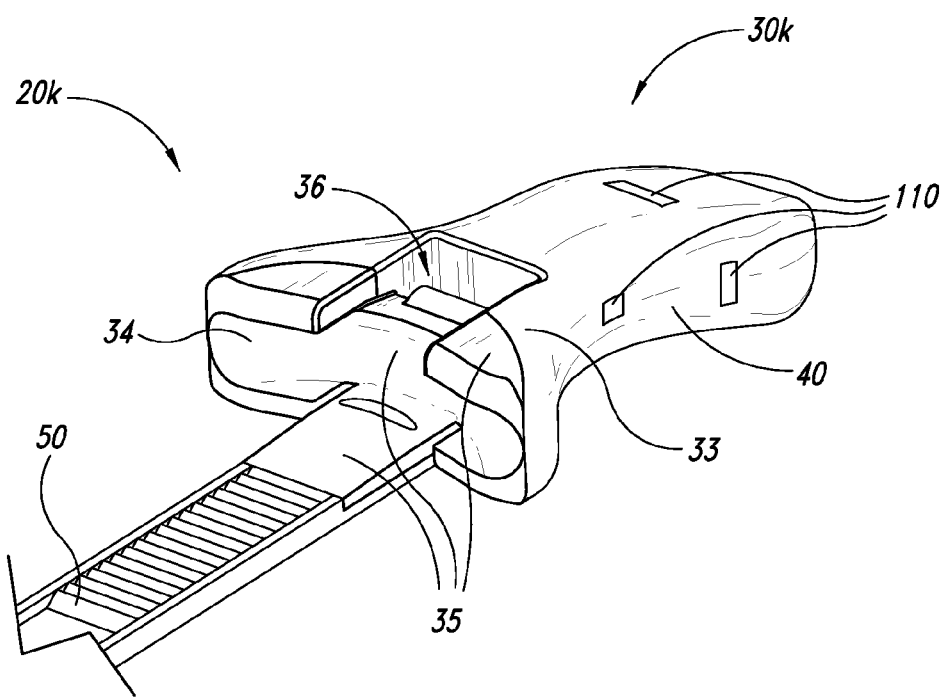
FIG. 8 is a partial isometric view of a transponder device according to one embodiment
Figure 9:
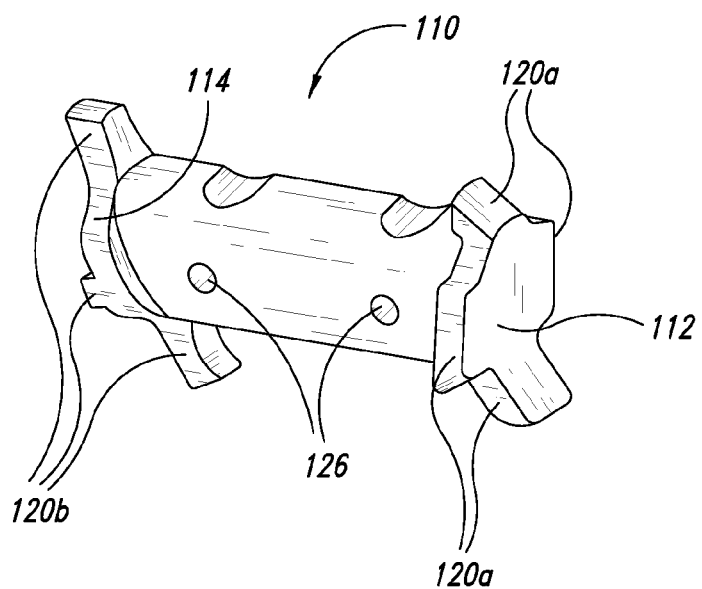
FIG. 9 is an isometric view of a framework enclosing a transponder according to one embodiment.

In some embodiments, the housing 30k of the transponder device may include a compliant overmold 35 that interfaces with at least a portion of the body 33. The compliant overmold 35 may be positioned proximate where the housing 30k is attachable to a surgical implement and include an implement receiving cavity 34 formed therein, as shown in FIG. 8. The implement receiving cavity 34 is sized to at least partially receive a portion of a surgical implement when the housing 30k is attached thereto. The compliant overmold 35 is resilient such that it partially deforms when the implement receiving cavity 34 engages the surgical implement, thus ensuring a more secure fit with the surgical implement and preventing the housing 30k from shifting during use. In other embodiments, the housing 30k may not include a compliant overmold 35, and may have an implement receiving cavity formed in the body 33 of the housing 30k for receiving a portion of the surgical implement.

According to one embodiment, an injection molded housing 30k is provided having a non-metallic framework 110 that substantially encloses a transponder circuit 23, a non-metallic body 33 which at least partially surrounds the framework 110 and which completely surrounds the transponder circuit 23, and a compliant overmold 35 that interfaces with at least a first portion of the body 33. The framework 110 may be a first shot of an injection molded material, such as various thermoplastic and thermosetting plastic materials. The body 33 may be a second shot of injection molded material that is the same or different than the injection molded material of the first shot, and the compliant overmold 35 may be a third shot of an injection molded material that has elastomeric properties. In one embodiment, the framework 110 and body 33 are formed of bio-inert, high service temperature plastic, such as those made under the trade names Noryl™, particularly grade HNA055, and Zytel™, particularly grade SC310 NC010, and the compliant overmold 35 is formed of bio-inert, high service plastic having elastomeric properties, such as those made under the trade name Santoprene™, particularly grades 181-55MED or 8281-35MED.

As illustrated in FIG. 8, the transponder device 20k may include various additional features for attaching the housing 30k to a surgical implement and/or facilitating the operation of the surgical implement when attached thereto. For example, the body 33 may include a saddle-shaped finger support surface 40 sized and configured to receive a finger of a user and provide additional leverage to operate the surgical implement. As another example, the body 33 may include an elongated strap 50 formed integrally therewith and a strap receiving cavity 36, wherein the strap 50 is dimensioned to encircle a portion of a surgical implement and the strap receiving cavity 36 sized to receive at least a portion of the strap 50 to attach the housing 30k to the surgical implement. In this manner, the transponder device may be attached to various conventional surgical implements with little effort and in a manner that enhances operation of the same.

The transponder device 20k illustrated in FIG. 8 may be manufactured using a multi-stage fabrication process, such as, for example, a multi-stage injection molding process. As can be appreciated from FIGS. 9 and 10, a rigid or semi-rigid framework 110 of the device 20k may be formed around a transponder 22 in a first stage of a fabrication process by injecting a first shot of injection molded material into a first mold cavity having a transponder 22 positioned therein. The framework 110, and hence transponder 22, may then be retained in a cavity 131 of a second mold 130 for subsequent formation of the rigid body 33 of the transponder housing 30k, as illustrated in FIG. 11. Projections 120 extending outwardly from the framework 110 position the transponder 22 within an interior region of the mold cavity 131 (i.e., inwardly from an exterior surface 136 of the mold cavity 131). The rigid body 33 is then formed in a second stage of the fabrication process by injecting a second shot of injection molded material into the second mold, the body 33 at least partially surrounding the framework 110 and completely surrounding the transponder 22. Next, a compliant overmold 35 (FIG. 8) that interfaces with a portion of the body 33 may be formed via a third shot of an injection molded material in a third stage of the fabrication process to complete the transponder device 20k. The injection molded materials of the first and second shots may be the same material or may be different materials. The third shot may be a different material than the first and the second shots, and preferably has elastomeric properties, such as, for example, those typical of injection molded thermoplastic elastomers.

As described above, the transponder device 20k may be manufactured to include various additional features for attaching the housing 30k to the surgical implement. For example, the housing 30k may include a strap 50 for attaching the housing 30k to the implement or may include an adhesive layer on at least a portion of the housing 30k for adhering the housing 30k to the implement. In some embodiments, a portion of the housing 30k may be formed of a material having tackifier additives such that the portion of the resultant housing 30f is tacky and may adhere to the surgical implement without the application of a separate adhesive layer. These and other various attachment mechanisms may be used to fixedly or removably secure the device 20k to the surgical implement.

Advantageously, transponder devices 20 that are removably attachable may allow the transponder devices 20 to be moved between various surgical implements 14. For example, such may allow transponder devices 20 to be used on new implements 14 after older implements 14 are disposed or while older implements 14 are being refurbished (e.g., sharpened). In some embodiments, the surgical implements 14 may be provided to the end user (e.g., hospital, surgeon or other medical services provider) with the transponder device 20 attached. In other embodiments, the end user may attach or couple the transponder devices 20 to the surgical implements 14, and/or may remove the transponder devices 20 from the surgical implements 14. Such may allow a manufacturer, distributor or end user to produce and/or stock one set of surgical implements 14 which may be customized with an appropriate transponder based on the particular needs or system of the end user.

Figure 12:
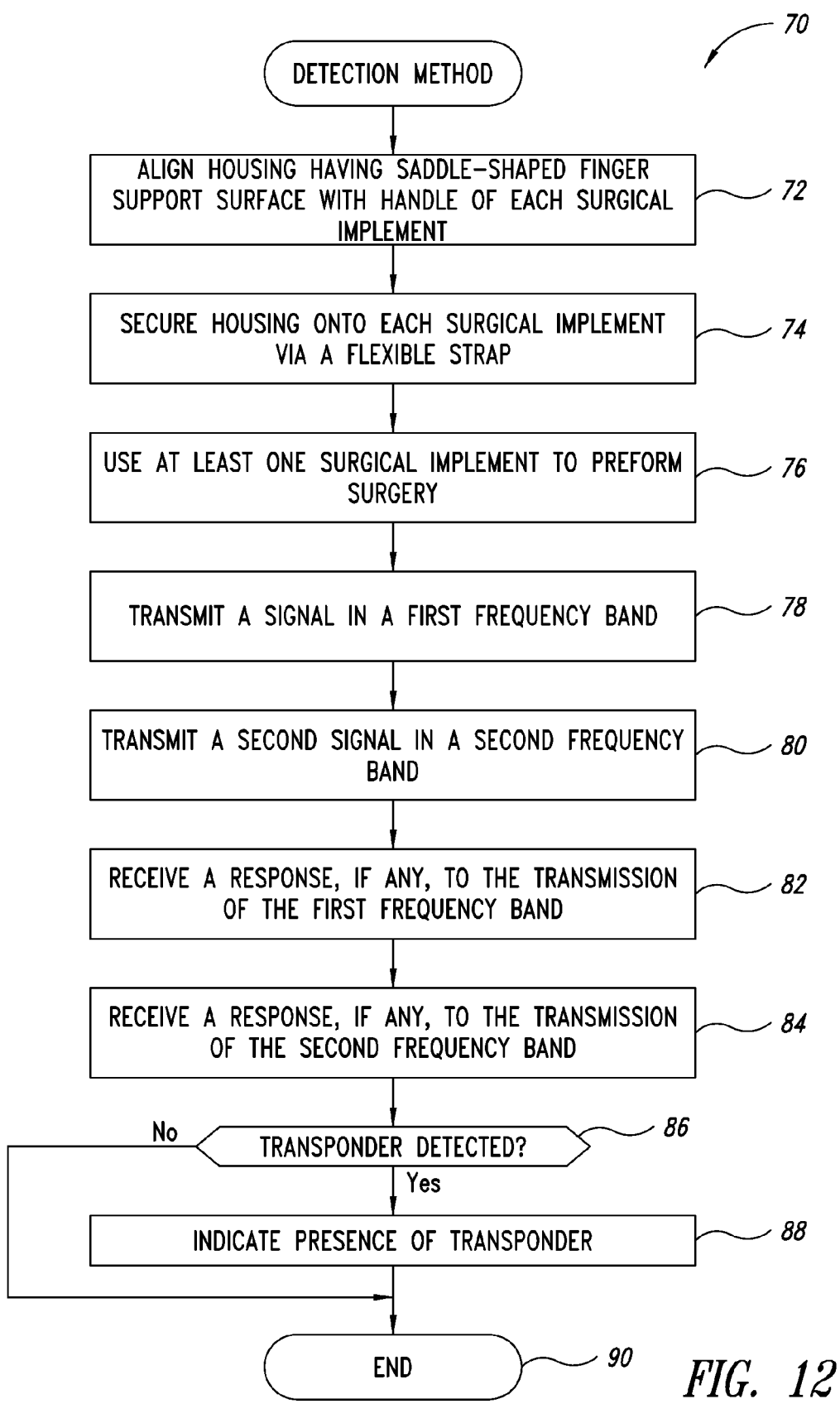
FIG. 12 is a flow diagram of a method for detecting the presence of a foreign object according to one illustrated embodiment.

FIG. 12 is a flow diagram of a method 70 for detecting the presence of an object according to one embodiment.

The method begins at 72, where a transponder housing 30e, 30k having a saddle-shaped finger support surface 40 and a implement receiving cavity 34 is aligned with a handle 16 of each of one or more rigid surgical implements 14 such that when the handle 16 is received in the implement receiving cavity 34, a wireless transponder 22 enclosed within the housing 30e, 30k is at least 1 millimeter from the handle, a central plane of the housing 30e, 30k is substantially co-planar with a central plane of the handle 16, and the finger support surface 40 is oriented to receive a finger of a user when the user is utilizing the surgical implement 14. After aligning the transponder housing 30e, 30k, the housing is secured onto the handle 16 via a flexible strap 50 at 74. In other embodiments, the housing 30e may be secured onto the handle 16 via mechanisms, structures and/or substances in addition to or in lieu of the flexible strap 50, such as, for example, snaps, clips, rivets, hook and loop fasteners and/or adhesives. In addition, in some embodiments, a transponder device 20 may also be carried, attached, secured or coupled to other surgical implements, such as other rigid implements and non-rigid implements, like sponges and gauze. After securing the transponder housing 30e, 30k, at least one of the rigid surgical implements 14 is used to perform the surgery at 76. In some embodiments, some or all of the surgical implements 14 may not be used during surgery. For example, the operating room may have additional surgical implements 14 that are used in case there are complications or surgical implements of various sizes may be present so that the right one can be used for the task at hand.

After the use of the surgical implements 14, a signal is transmitted in a first frequency band at 78. Subsequently, a second signal is transmitted in a second frequency band at 80. A response may be received, if any, to the transmission of the first frequency band at 82. A response may be received, if any, to the transmission of the second frequency band at 84. At 86, based on the responses received, it is determined if a transponder 22 has been detected. If so, the presence of a transponder 22 may be indicated at 88 and if not, the method ends at 90. The presence may be indicated in a number of manners, including but not limited to, visually on a display, lighting up LEDs on the detection/interrogation device, or by emitting a sound. After indicating the presence of the transponder 22, the method ends.

In some embodiments, some of the acts may be performed in different orders. For example, the response to the first frequency band, if any, may be received before the transmission of the second signal in the second signal band. In addition, in one embodiment, one or more of the surgical implements 14 may be sterilized (e.g., by autoclaving) with the attached transponder device 20. In other embodiments, the transponder device 20 may be removed from the surgical implement 14 prior to sterilizing, disposal and/or refurbishing of the surgical implement 14.

FIGS. 13-17 illustrate additional embodiments of transponder devices 20 to mark surgical implements 14, and more particularly surgical implements 14 having an elongated handle portion 96 and a finger ring portion 98, such as, for example, surgical scissors. In various embodiments, the transponder device 20 includes a housing 30 that retains a transponder (not shown) and fixedly spaces the transponder at least about 1 millimeter and preferably at least about 2 millimeters from any metallic portion of the surgical implement 14 when the transponder device 20 is attached or otherwise coupled to the surgical implement 14. In the embodiments shown in FIGS. 13-17 the housings 30 are illustrated as casings, the casings are formed or fabricated with a transponder (not shown) retained therein during the fabrication.

Figure 13:
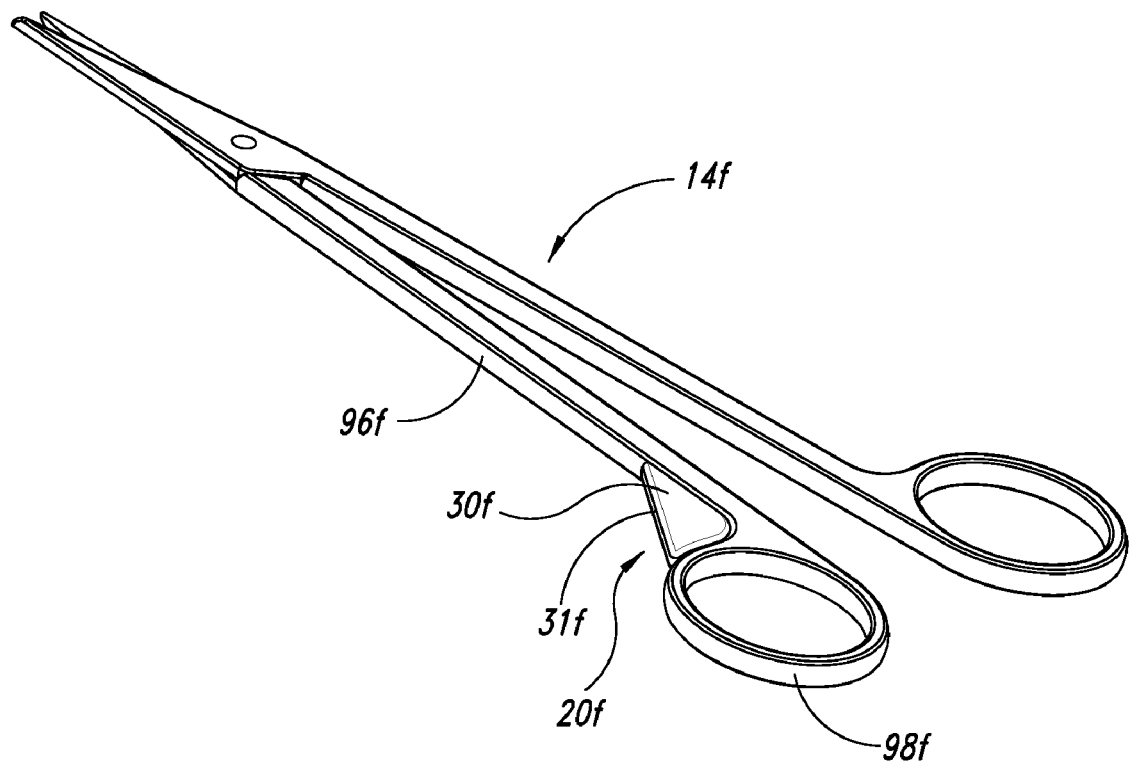
FIG. 13 is an isometric view of a transponder device coupled to a surgical implement according to one embodiment.

FIG. 13 illustrates one embodiment of a transponder device 20f having a housing 30f in the form of a casing for attaching to a portion of a surgical implement 14f, such as surgical scissors. The casing may be rigid or may be compliant. The transponder device 20f may be attached to the surgical implement 14f by adhering the housing 30f to the surgical implement with adhesive or glue. For example, the housing 30f may include a pressure-sensitive adhesive layer with a removable backing. In this manner, the transponder device 20f may be provided separately from the surgical implement 14f and subsequently applied to a surgical implement 14f prior to use by removing the adhesive backing and pressing the housing 30f onto the surgical implement 14f. In other embodiments, a portion of the housing 30f may be formed of a polymer using tackifier additives such that the portion of the housing 30f is tacky and may adhere to the surgical implement 14f without the application of a separate adhesive layer. In other embodiments, the housing 30f may be attached or coupled to the surgical implement 14f with other attachment mechanisms or structures, such as, for example, a strap or band. In some embodiments, a strap or band that is integral with the housing 30f may encircle a portion of the surgical implement and attach itself to the housing 30f using engagement structures, such as, for example, teeth, detents, barbs, snaps, other fasteners or the like. The strap or band may be employed in place of, or in addition to, an adhesive layer or adhering portion of the housing 30f.

The transponder housing 30f is advantageously configured to engage the portion of the surgical implement 14f proximate where an elongated handle portion 96f and a finger ring portion 98f of the surgical implement 14f converge. More particularly, the housing 30f has a perimeter with a first portion which is arcuate to accommodate an upper portion of an outer diameter of the finger ring portion 98f. A second portion is substantially flat and straight to accommodate the elongated handle portion 96f, and a rounded corner portion between the first and second portions is provided to accommodate the corner of the surgical implement 14f where the elongated handle portion 96f and the finger ring portion 98f converge. In this manner, physical contact over a relatively large surface is provided, thereby allowing the device 20f to be securely attached to the surgical implement 14f. A third portion that extends between the first and second portions is sized to be relatively straight and angled to minimize potential interference with a hand of a user during operation of the implement 14f. The third portion may also be configured to include a stabilizing surface 31f positioned to receive a finger of a user when operating the surgical implement 14f. Accordingly, a user can grasp and operate the surgical implement 14f and stabilize or steady the same by engaging the stabilizing surface 31f with a finger of the user's hand. The housing 30f further includes a first upper surface offset from a second opposing lower surface such that a thickness of the housing 30f is about equal to a thickness of the portion of the surgical implement 14f where the device 20f is attached, further minimizing potential interference with a hand of a user during operation of the implement 14f. Where compliant, the transponder housing 30f or portions thereof may provide added comfort to the user, while still providing leverage in operating the surgical implement 14f.

Although the illustrated housing 30f is shown as a unitary casing having a transponder (not shown) enclosed therein, it is contemplated that the housing 30f may be fabricated in a number of different ways and/or forms. For example, in some embodiments, the housing 30f may be fabricated as a shell structure, such as a clam shell structure, that includes pre-existing cavities that cooperate when closed around a transponder to retain the transponder within the housing. In other embodiments, the housing 30f may be a rigid body having a pre-existing cavity sized to receive the transponder. In this manner, the transponder may be inserted in the housing 30f after the housing 30f is fabricated. The rigid body may have a compliant over coat.

Figure 14:
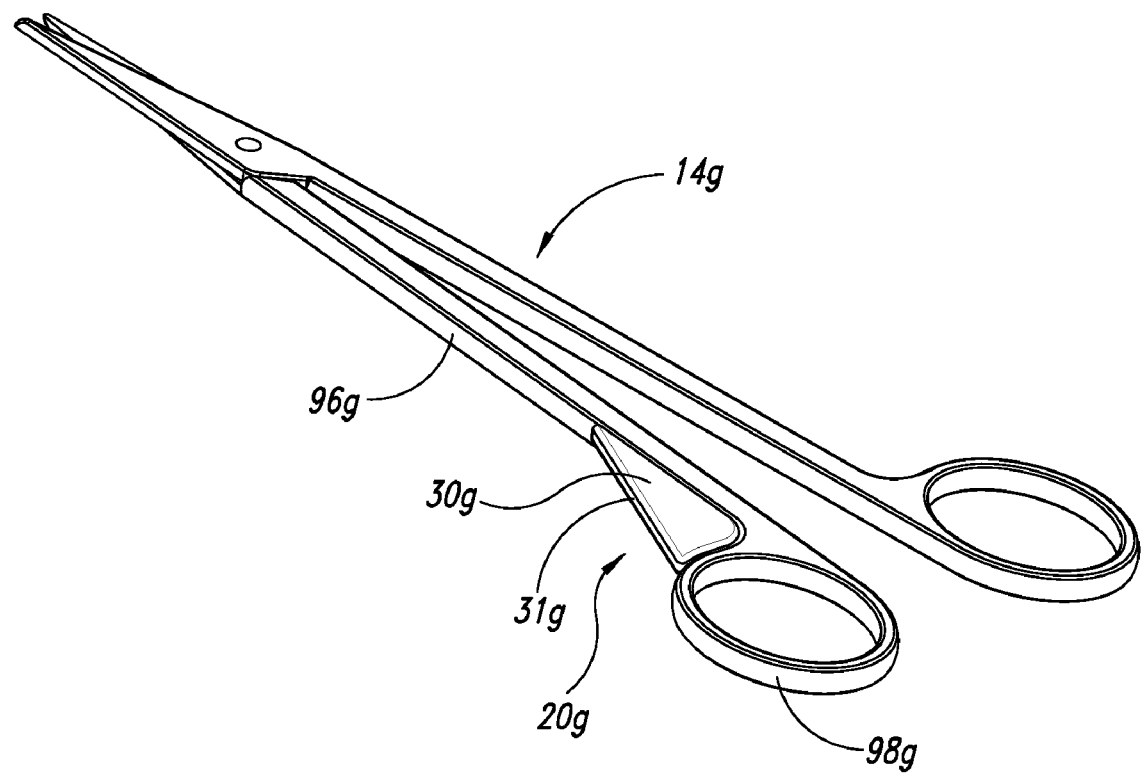
FIG. 14 is an isometric view of a transponder device coupled to a surgical implement according to one embodiment.
Figure 15:
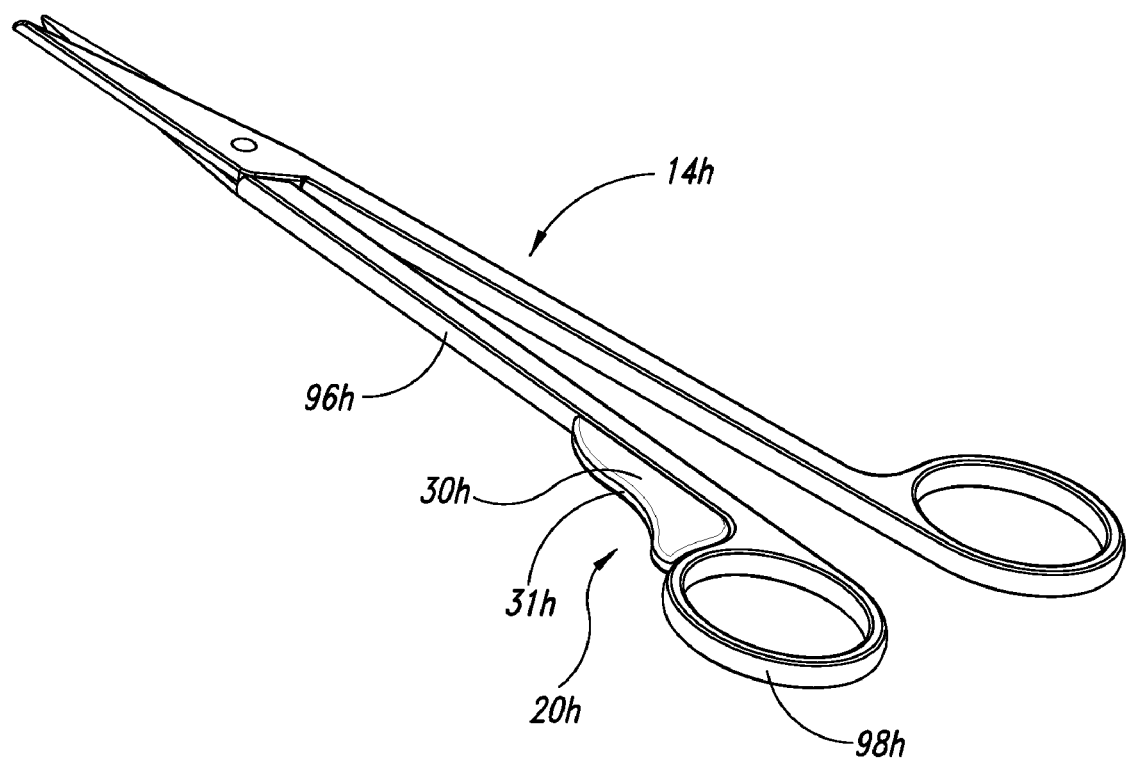
FIG. 15 is an isometric view of a transponder device coupled to a surgical implement according to one embodiment.
Figure 16:
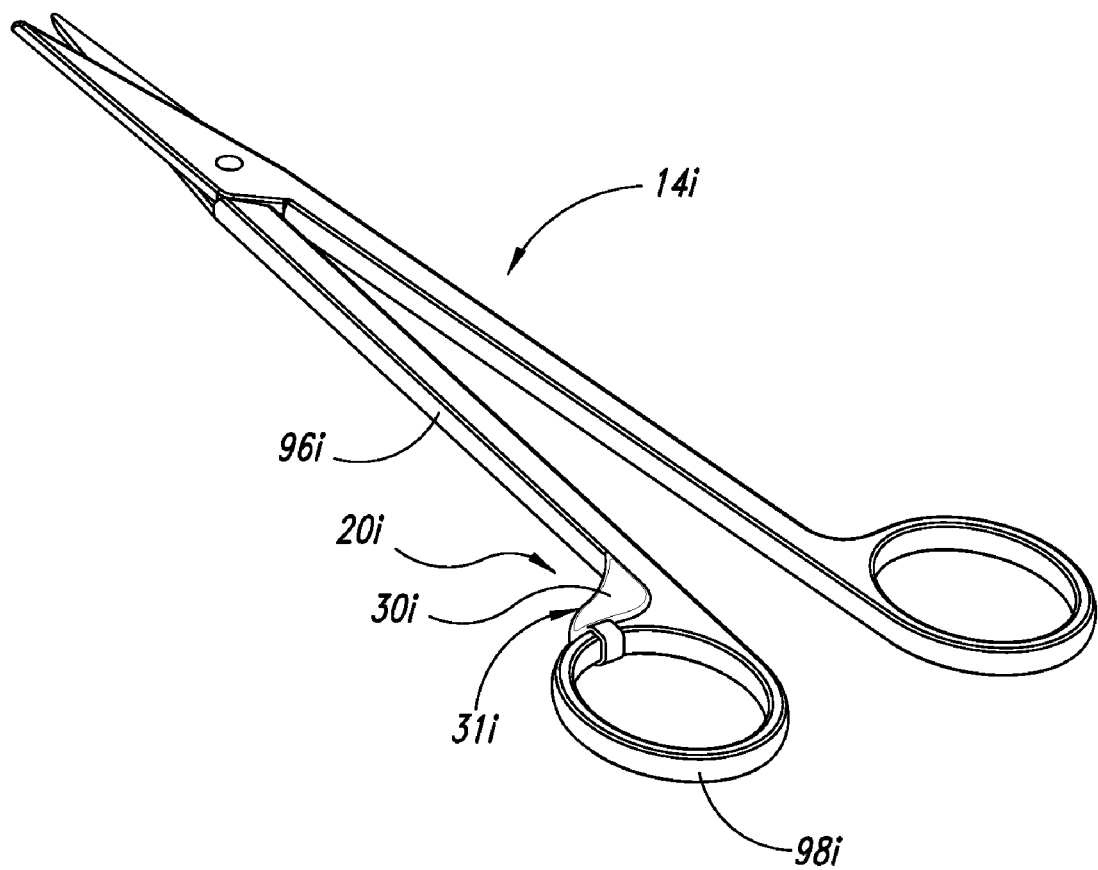
FIG. 16 is an isometric view of a transponder device coupled to a surgical implement according to one embodiment.

Like the embodiments described above with respect to FIG. 13, the embodiments shown in FIGS. 14-16 may similarly include a variety of housing structures and are likewise advantageously configured to engage a portion of a surgical implement 14 proximate where an elongated handle portion 96 and a finger ring portion 98 of the surgical implement 14 converge. Each of the embodiments shown in FIGS. 14-16 thus include a housing 30 having a perimeter with a first portion which is arcuate to accommodate an upper portion of an outer diameter of the finger ring portion 98, a second portion that is substantially flat and straight to accommodate the elongated handle portion 96, and a rounded corner portion between the first and second portions to accommodate the corner of the surgical implement 14 where the elongated handle portion 96 and the finger ring portion 98 converge. Likewise, the embodiments shown in FIGS. 14-16 each include a stabilizing surface 31 located on a third portion of the perimeter between the first and second portions such that the stabilizing surface 31 is positioned to receive a finger of a user when operating the surgical implement 14.

FIGS. 14-16 further illustrate transponder devices 20 that vary in size and shape from the device 20f shown in FIG. 13 and illustrate various attachment structures and mechanisms. For example, FIG. 14 illustrates a transponder device 20g that includes a housing 30g where the second portion of the perimeter extends a substantial length of the elongated portion 96g of the surgical implement 14g to provide a relatively larger surface area for more securely attaching the device 20g to the surgical implement 14g.

As another example, FIG. 15 illustrates a transponder device 20h wherein the stabilizing surface 31h located on the perimeter of the housing 30h includes a concave portion between two convex portions to more comfortably receive a user's finger when operating the implement 14h. The concave portion of the stabilizing surface 31h transitions smoothly from the upper surface of the housing 30h to the opposing lower surface such that the concave portion has a saddle-shape. A user may engage this concave portion of the stabilizing surface 31h during use to more accurately control and stabilize the implement 14h.

FIG. 16 illustrates a relatively small transponder device 20i. The transponder device 20i, like the embodiment described immediately above, includes a housing 30i having a stabilizing surface 31i with a concave portion adapted to more comfortably receive a user's finger during operation of the implement 14i. The illustrated device 20i further includes a strap or band that may be employed in place of, or in addition to, an adhesive carried by the perimeter to secure or couple the device 20i to the implement 14i. In some embodiments, the strap or band may include one or more engagement structures, such as, for example, teeth, detents, barbs, snaps, or other fastener or the like, that are adapted to cooperate with complimentary engagement structures on the housing 30i to secure the device 20i to the surgical implement 14i. The strap or band may be formed as an integral or a unitary portion of the transponder housing 30i, or may be separate or distinct therefrom. The strap may be fixedly or removably secured to the transponder housing 30i and may be attached manually or with the aid of a tool (not shown).

Figure 17:
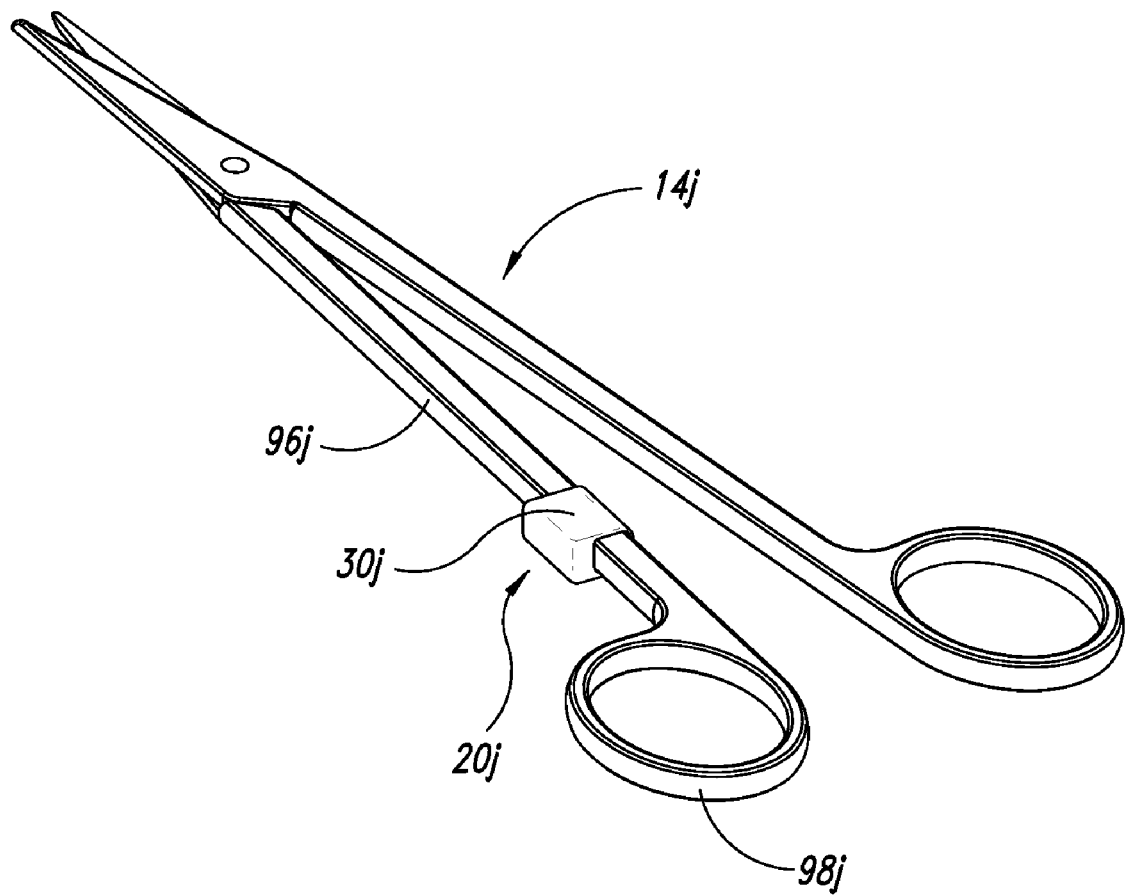
FIG. 17 is an isometric view of a transponder device coupled to a surgical implement according to one embodiment.

FIG. 17 illustrates yet another embodiment of a transponder device 20j for marking surgical implements, and in particular a surgical implement 14j having elongated handle portions 96j for operating the implement, such as, for example surgical scissors. The device 20j includes a relatively small housing 30j having an implement receiving portion configured to engage an elongated handle portion 96j of the surgical implement 14j and retains a transponder therein. The transponder receiving portion is configured with respect to the implement receiving portion to extend generally perpendicularly from the side of the elongated handle portion 96j and position the transponder such that a longitudinal length of the transponder is substantially parallel with the elongated handle portion 96j. Furthermore, the transponder is retained with respect to the implement receiving portion so as to space the transponder at least about 1 millimeter from any portion of the surgical implement 14j when the housing 30j is attached to the elongated handle portion 96j of the surgical implement 14j. The housing 30i may be fabricated with the transponder integrally therein. Alternatively, the transponder may be received in the housing 30j subsequent to fabrication of the housing 30j, for example, in a pre-existing cavity thereof. The device 20j is particularly adapted to closely engage the elongated handle portion 96j of the surgical implement remote from the finger ring portion 98j. In this manner, the transponder device 20j is particularly well adapted to attach to a surgical implement 14j without interfering with the operation of the implement 14j or otherwise being positioned to interfere with a user's ability to grasp and operate the implement 14j. In addition, although the transponder device 20j of FIG. 17 is illustrated as being oriented away from the surgical implement 14j, in some embodiments, the device 20j may be configured to attach to a surgical implement such that the housing 30j positions the transponder between opposing elongated handle portions thereof. In such embodiments, the transponder device 20j is particularly suited to attach to surgical implements which, during normal operation, include a space between opposing handle portions sufficiently large to receive the transponder housing, such as, for example, some hemostats.

The transponder device 20j shown in FIG. 17 is attachable to a portion of a surgical implement 14j via adhesive and/or other attachment mechanisms or structures, such as snaps, clips, a strap, band or other fastener. For example, the implement receiving portion may include an adhesive layer, such as a pressure sensitive adhesive layer, to bond the transponder device 20j to the elongated handle portion 96j of the surgical implement 14j. In some embodiments, the device 20j may include resilient snaps or clips for attaching the transponder device 20j to the handle portion 96j of the surgical implement 14j. In still other embodiments, the device 20j may include a strap, band or other fastener. The strap or band may be an elastomeric material, such as, for example, an elastomeric fabric, or polymer, or an elastomeric metal (e.g., Nitinol) or other shape memory material. In some embodiments, the strap or band may be sufficiently resilient to stretch over the finger ring portion 98j of the surgical implement and return to an undeformed shape to securely receive the elongated handle portion 96j of the surgical implement 14j. In other embodiments, the strap or band may include one or more engagement structures, such as, for example, teeth, detents, barbs, snaps, other fasteners or the like, that are adapted to cooperate with complimentary engagement structures on the housing 30j to secure the housing 30j to the surgical implement 14j. The strap or band may be formed as an integral or a unitary portion of the transponder housing 30j, or may be separate or distinct therefrom. In addition, the strap may be fixedly or removably secured to the transponder housing 30j and may be attached manually or with the aid of a tool (not shown).

The above description of illustrated embodiments, including what is described in the Abstract, is not intended to be exhaustive or to limit the various embodiments to the precise forms disclosed. Although specific embodiments of and examples are described herein for illustrative purposes, various equivalent modifications can be made without departing from the spirit and scope of the disclosure, as will be recognized by those skilled in the relevant art.

The teachings provided herein can be applied to other metallic implements, other types of transponders, and other interrogation and detection systems. For instance, the transponder device may be used to mark implements anytime detection of the presence of marked objects is desirable in a confined area, not just during surgery. For example, it may be used to make sure marked tools are not left inside a machine (e.g., vehicle, such as aircraft, truck, or car, copy machine, etc.) after manufacture or maintenance is performed. In at least some embodiments, the transponder housing may be utilized to mark objects to determine the removal of a marked implement from a confined area, such as kitchen shears from a kitchen. In such an embodiment, an interrogation device, for example, may be placed proximate to a door of the confined area.

In addition, a housing may be manufactured and distributed for tagging objects without a transponder currently attached or installed therein. Advantageously, the housing can then be used to place a transponder compatible with a particular detection and interrogation system at a subsequent time, including by the end-user.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, if any, including but not limited to U.S. Pat. No. 6,026,818, issued Feb. 22, 2000; U.S. Patent Publication No. US 2004/0250819, published Dec. 16, 2004; U.S. patent application Ser. No. 11/759,141, filed Jun.

6, 2007; U.S. patent application Ser. No. 12/038,593, filed Feb. 27, 2008; and U.S. patent application Ser. No. 12/046,396, filed Mar. 11, 2008 are incorporated herein by reference, in their entirety. Aspects of the embodiments can be modified, if necessary, to employ concepts of the various patents, applications and publications to provide yet further embodiments.

These and other changes can be made in light of the above-detailed description. In general, in the following claims, the terms used should not be construed to limit the invention to the specific embodiments disclosed in the specification and the claims, but should be construed to include all possible embodiments along with the full scope of equivalents to which such claims are entitled. Accordingly, the invention is not limited by the disclosure.

The invention claimed is:

1. A device to mark surgical implements, the device comprising:
a flexible strap;
a housing attachable to a portion of a surgical implement, the housing including a transponder receiving cavity, an implement receiving cavity sized to receive a portion of the surgical implement, a strap receiving cavity sized to receive at least a portion of the strap, and a saddle-shaped finger support surface sized and configured to receive a finger of a user and provide additional leverage for operating the surgical implement when the housing is attached to the portion of the surgical implement via the strap and the implement receiving cavity; and
a transponder retained in the transponder receiving cavity, and
wherein the housing includes a base substrate, a first overmold portion that forms the implement receiving cavity and a second overmold portion that retains the transponder within the transponder receiving cavity, and the first overmold portion and the second overmold portion comprise a material that is different from a material of the base substrate.

2. The device of claim 1 wherein the first overmold portion includes an indentation proximate a base of the strap where the strap is fixed to the housing such that a bend radius of the strap is reduced relative to an identically sized strap without an indentation.

3. The device of claim 1 wherein the first overmold portion includes a raised surface proximate a base of the strap that substantially conforms with a contour of a handle of the surgical implement when the housing is attached thereto.

4. A device to mark surgical implements, the device comprising:
a flexible strap; and
a housing attachable to a portion of a surgical implement, the housing including a transponder receiving cavity sized to receive a transponder, an implement receiving cavity sized to receive a portion of the surgical implement, a strap receiving cavity sized to receive at least a portion of the strap, and a saddle-shaped finger support surface sized and configured to receive a finger of a user and provide additional leverage for operating the surgical implement when the housing is attached to the portion of the surgical implement via the strap and the implement receiving cavity, wherein the housing includes a base substrate and a first overmold portion that forms the implement receiving cavity, and wherein a projection of the first overmold portion extends beyond an interior profile of a handle of the surgical instrument to provide a gradual transition from the interior profile of the handle to a surface of the strap when the housing is attached to the handle.

5. The device of claim 1 wherein the first overmold portion and the second overmold portion are each composed of an elastomeric material.

6. The device of claim 1 wherein the strap receiving cavity provides a void proximate a lower surface of the housing such that an end of the strap does not protrude beyond the lower surface when the strap is received in the strap receiving cavity and trimmed to a final length.

7. The device of claim 1 wherein the transponder receiving cavity is spaced at least about 1 millimeter from any portion of the surgical implement when the housing is attached to the surgical implement via the strap.

8. The device of claim 1 wherein the strap and the housing form a unitary structure.

9. A transponder device comprising:
a housing having a base substrate and an overmold portion, the base substrate containing a transponder receiving cavity;
attachment means for attaching the housing to a portion of a surgical implement; and
a wireless transponder received in the transponder receiving cavity, and
wherein the overmold portion of the housing includes an indentation proximate a base of the strap where the strap is fixed to the housing such that a bend radius of the strap is reduced relative to an identically sized strap without an indentation.

10. The transponder device of claim 9 wherein the housing positions the wireless transponder at least 1 millimeter from the surgical implement when attached to the portion of the surgical implement.

11. The transponder device of claim 9 wherein the overmold portion retains the transponder in the base substrate.

12. The transponder device of claim 9 wherein the overmold portion includes an implement receiving cavity.

13. The transponder device of claim 12 wherein the housing further includes a saddle-shaped finger support surface sized and configured to receive a finger of a user and provide additional leverage for operating the surgical implement when the housing is attached to the portion of the surgical implement via the implement receiving cavity.

14. The transponder device of claim 9 wherein the overmold portion includes a first overmold location and a second overmold location, the first overmold location including an implement receiving cavity and the second overmold location retaining the transponder in the base substrate.

15. The transponder device of claim 9 wherein the overmold portion comprises a material different from a material of the base substrate.

16. The transponder device of claim 9 wherein the overmold portion is composed of an elastomeric material.

17. A transponder device comprising:
a housing having a base substrate and an overmold portion, the base substrate containing a transponder receiving cavity;
attachment means including a strap and a detent mechanism integral to the housing for attaching the housing to a portion of a surgical implement; and
a wireless transponder received in the transponder receiving cavity, and
wherein the overmold portion of the housing includes a raised surface proximate a base of the strap that substantially conforms with an interior contour of a handle of the surgical implement when the housing is attached thereto.

18. The transponder device of claim 17 wherein the overmold portion includes an indentation in the raised surface such that a bend radius of the strap is reduced relative to an identically sized strap without an indentation.

19. A transponder device comprising:
a housing having a base substrate and an overmold portion, the base substrate containing a transponder receiving cavity;
attachment means including a strap and a detent mechanism integral to the housing for attaching the housing to a portion of a surgical implement; and
a wireless transponder received in the transponder receiving cavity, and
wherein the overmold portion of the housing includes at least one projection extending beyond an interior profile of a handle of the surgical instrument to provide a gradual transition from the interior profile of the handle to a surface of the strap when the housing is attached to the handle.

20. A transponder device comprising:
a housing having a base substrate and an overmold portion, the base substrate containing a transponder receiving cavity;
attachment means including a strap and a detent mechanism integral to the housing for attaching the housing to a portion of a surgical implement; and
a wireless transponder received in the transponder receiving cavity, and
wherein the housing further includes a strap receiving cavity sized to receive at least a portion of the strap, the strap receiving cavity providing a void proximate a lower surface of the housing such that an end of the strap does not protrude beyond the lower surface when the strap is received in the strap receiving cavity and trimmed to a final length.

21. A method for manufacturing a device to mark implements comprising:
molding a base substrate, the base substrate including a transponder receiving cavity sized to receive a transponder, a flexible strap, a strap receiving cavity sized to receive at least a portion of the strap, and a saddle-shaped finger support surface sized and configured to receive a finger of a user and provide additional leverage for operating an implement when the base substrate is attached to a portion of the implement;
forming an overmold portion with an implement receiving cavity such that a surface of the implement receiving cavity and the finger support surface converge proximate a tip of the device;
inserting the transponder in the transponder receiving cavity; and
retaining the transponder within the transponder receiving cavity.

22. The method according to claim 21 wherein retaining the transponder within the transponder receiving cavity includes retaining the transponder within the transponder receiving cavity by covering a portion of the transponder with the overmold portion.

23. The method according to claim 21 wherein retaining the transponder within the transponder receiving cavity includes retaining the transponder within the transponder receiving cavity by covering the transponder with a cap.

24. A transponder device selectively attachable to surgical implements, the transponder device comprising:
a transponder circuit;
a non-metallic framework that substantially encloses the transponder circuit, the framework having a number of outward extending projections; and
a non-metallic body which at least partially surrounds the framework and which completely surrounds the transponder circuit, wherein the outward extending projections of the framework position the transponder circuit inwardly from an exterior surface of a mold used to form the body during a fabrication of the transponder device.

25. The transponder device of claim 24 wherein the framework is elongated having a first end and a second end, and the framework includes at least two pairs of opposed outward extending projections, one pair at each of the first and the second ends.

26. The transponder device of claim 24 wherein the framework is completely received in the body.

27. The transponder device of claim 24, further comprising:
an encapsulant that encapsulates the transponder circuit and which is surrounded by the framework.

28. The transponder device of claim 24, further comprising:
a compliant overmold that interfaces with at least a first portion of the body.

29. The transponder device of claim 28 wherein the compliant overmold includes an implement receiving cavity formed therein, the implement receiving cavity sized to at least partially receive a portion of a surgical implement.

30. The transponder device of claim 24 wherein the framework is a first shot of an injection molded material.

31. The transponder device of claim 30 wherein the body is a second shot of an injection molded material.

32. The transponder device of claim 31, further comprising:
a third shot of an injection molded material that forms a compliant overmold that interfaces with at least a first portion of the body.

33. The transponder device of claim 32 wherein the third shot of injection molded material is a different type of material from the second shot of injection molded material.

34. The transponder device of claim 33 wherein the third shot of injection molded material is an elastomeric material.

35. The transponder device of claim 24 wherein the body includes a saddle-shaped finger support surface, the finger support surface sized and configured to receive a finger of a user and provide additional leverage to operate a surgical implement when the transponder device is attached to the surgical implement.

36. The transponder device of claim 24 wherein the body includes an elongated strap extending therefrom, the strap dimensioned to encircle a portion of a surgical implement to attach the transponder device to the surgical implement.

37. The transponder device of claim 36 wherein the body includes a strap receiving cavity formed therein, the strap receiving cavity sized to receive at least a portion of the strap therethrough.

38. A transponder device selectively attachable to surgical implements, the transponder device comprising:
a transponder circuit;
a framework having a number of outward extending projections that space the transponder circuit from a surface that forms a cavity of a mold in the shape of a body;
the body, which body at least partially surrounds the framework and which completely surrounds the transponder circuit; and
a compliant overmold interfacing with at least a first portion of the body.

39. The transponder device of claim 38 wherein the framework is a first shot of an injection molded material, the body is a second shot of an injection molded material, and the compliant overmold is a third shot of an injection molded material.

40. The transponder device of claim 38 wherein the body includes a saddle-shaped finger support surface, the finger support surface sized and configured to receive a finger of a user and provide additional leverage to operate a surgical implement when the transponder device is attached to a surgical implement.

41. The transponder device of claim 38 wherein the body includes an elongated strap extending therefrom and a strap receiving cavity formed therein, the strap dimensioned to encircle a portion of a surgical implement and the strap receiving cavity sized to receive at least a portion of the strap therethrough, to attach the transponder device to the surgical implement.

42. The transponder device of claim 38 wherein the compliant overmold includes an implement receiving cavity formed therein, the implement receiving cavity sized to at least partially receive a portion of a surgical implement.

43. A method for manufacturing a transponder device attachable to surgical implements, the method comprising:

forming a non-metallic framework around a transponder circuit, the framework including a number of outward extending projections;

retaining the framework in a mold cavity, wherein the outward extending projections of the framework position the transponder circuit inwardly from an exterior surface of the mold cavity;

forming via the mold cavity a non-metallic body which at least partially surrounds the framework and which completely surrounds the transponder circuit; and forming a compliant overmold that interfaces with at least a first portion of the body, the compliant overmold including an implement receiving cavity sized to at least partially receive a portion of a surgical implement.

44. The method according to claim 43 wherein the framework is formed with a first shot of an injection molded material, the body is formed with a second shot of an injection molded material; and the compliant overmold is formed with a third shot of an injection molded material.

\* \* \* \* \*